US005872235A

United States Patent [19]

Chen et al.

[11] Patent Number: 5,872,235

[45] Date of Patent: Feb. 16, 1999

[54] NUCLEIC ACIDS ENCODING TUMOR MARKER

[75] Inventors: Lan Bo Chen, Lexington; Shideng Bao, Cambridge; Yuan Liu, Brookline, all of Mass.

[73] Assignee: Dana-Farber Cancer Institute, Inc., Boston, Mass.

[21] Appl. No.: 477,396

[22] Filed: Jun. 7, 1995

Related U.S. Application Data

[63] Continuation of Ser. No. 348,747, Dec. 1, 1994, abandoned, which is a continuation of Ser. No. 146,488, Oct. 29, 1993, abandoned.

[51] Int. Cl.[6] .......................... C12N 15/12; C12N 15/11

[52] U.S. Cl. .................. 536/23.5; 536/24.3; 536/24.31; 536/24.33

[58] Field of Search .............................. 536/23.5, 24.3, 536/24.31, 24.33

[56] References Cited

U.S. PATENT DOCUMENTS

| | | | |
|---|---|---|---|
| 5,444,164 | 8/1995 | Purchio et al. | 536/23.5 |
| 5,756,664 | 5/1998 | Amann et al. | 530/326 |

FOREIGN PATENT DOCUMENTS

| | | |
|---|---|---|
| 0549107 | 6/1993 | European Pat. Off. . |
| 0562508 | 9/1993 | European Pat. Off. . |
| WO 9304198 | 3/1993 | WIPO . |
| WO 9318176 | 9/1993 | WIPO . |

OTHER PUBLICATIONS

Takeshita et al. Biochem. J. 294:271–8, Aug. 1993.

Meyers et al., "Reverse Transcription and DNA Amplication by a *Thermus thermophilus* DNA Polymerase," *Biochemistry* 30:7661–7666 (1991).

Liang et al., "Differential Display of Eukaryotic Messenger RNA by Means of the Polymerase Chain Reaction," *Science* 257:967–971 (1992).

Welsh et al., "Arbitrarily primed PCT fingerprinting of RNA," *Nucleic Acid Research* 20:4965–4970 (1992).

Bao et al., "Identification and isolation of differentially expressed genes by palindromic PCR," *Molecular Biology of the Cell* 4:357A (1993).

Barnes, Human DNA ligasel cDNA: Cloning and functional expression in *Saccharomyces cerevisiae, Proc. Natl. Acad. Sci USA* 87:6679–6683 (1990).

Mao et al., "Molecular Characterization of the Human Interferon–γ Receptor: Analysis of Polymorphism and Glycosylation," *Journal of Interferon Research* 9:659–669 (1989).

Takeshita et al., "Osteoblast–specific factor 2: cloning of a putative bone adhesion protein with homology with the insect protein fasciclin 1," *Biochem. J.* 294:271–278 (1993).

Skonier et al., "cDNA Cloning and SEquence Analysis of βig–h3, a Novel Gene Induced in a Human Adenocarcinoma Cell Line after Treatment with Transforming Growth Factor–β," *DNA and Cell Biology* 11:511–522 (1992).

*Primary Examiner*—Elizabeth C. Kemmerer
*Attorney, Agent, or Firm*—Weingarten, Schurgin, Gagnebin & Hayes LLP

[57] ABSTRACT

The invention encompasses a novel tumor marker which is present on tumor cells and absent on corresponding normal cells, nucleic acid encoding the tumor marker, and a novel method of isolating DNA encoding the tumor marker or a gene which is differentially expressed in tissues.

6 Claims, 33 Drawing Sheets
(11 of 33 Drawing Sheets Filed in Color)

```
1/1                                     31/11
CTG ATC CAT GGG AAC CAG ATT GCA ACA AAT GGT GTT GTC CAT GTC ATT GAC CGT GTG CTT
 L   I   H   G   N   Q   I   A   T   N   G   V   V   H   V   I   D   R   V   L
61/21                                   91/31
ACA CAA ATT GGT ACC TCA ATT CAA GAC TTC ATT GAA GCA GAA GAT GAC CTT TCA TCT TTT
 T   Q   I   G   T   S   I   Q   D   F   I   E   A   E   D   D   L   S   S   F
121/41                                  151/51
AGA GCA GCT GCC ATC ACA TCG GAC ATA TTG GAG GCC CTT GGA AGA GAC GGT CAC TTC ACA
 R   A   A   A   I   T   S   D   I   L   E   A   L   G   R   D   G   H   F   T
181/61                                  211/71
CTC TTT GCT CCC ACC AAT GAG GCT TTT GAG AAA CTT CCA CGA GGT GTC CTA GAA AGG ATC
 L   F   A   P   T   N   E   A   F   E   K   L   P   R   G   V   L   E   R   I
241/81                                  271/91
ATG GGA GAC AAA GTG GCT TCC GAA GCT CTT ATG AAG TAC CAC ATC TTA AAT ACT CTC CAG
 M   G   D   K   V   A   S   E   A   L   M   K   Y   H   I   L   N   T   L   Q
301/101                                 331/111
TGT TCT GAG TCT ATT ATG GGA GGA GCA GTC TTT GAG ACG CTG GAA GGA AAT ACA ATT GAG
 C   S   E   S   I   M   G   G   A   V   F   E   T   L   E   G   N   T   I   E
361/121                                 391/131
ATA GGA TGT GAC GGT GAC AGT ATA ACA GTA AAT GGA ATC AAA ATG GTG AAC AAA AAG GAT
 I   G   C   D   G   D   S   I   T   V   N   G   I   K   M   V   N   K   K   D
421/141                                 451/151
ATT GTG ACA AAT AAT GGT GTG ATC CAT TTG ATT GAT CAG GTC CTA ATT CCT GAT TCT GCC
 I   V   T   N   N   G   V   I   H   L   I   D   Q   V   L   I   P   D   S   A
481/161                                 511/171
AAA CAA GTT ATT GAG CTG GCT GGA AAA CAG CAA ACC ACC TTC ACG GAT CTT GTG GCC CAA
 K   Q   V   I   E   L   A   G   K   Q   Q   T   T   F   T   D   L   V   A   Q
541/181                                 571/191
TTA GGC TTG GCA TCT GCT CTG AGG CCA GAT GGA GAA TAC ACT TTG CTG GCA CCT GTG AAT
 L   G   L   A   S   A   L   R   P   D   G   E   Y   T   L   L   A   P   V   N
601/201                                 631/211
AAT GCA TTT TCT GAT GAT ACT CTC AGC ATG GAT CAG
 N   A   F   S   D   D   T   L   S   M   D   Q
```

FIG. 3

TC1-DNA -> Genes

DNA Sequence 3126 b.p. gccaccatgtag . . . ctttctcgtgcc linear

```
  1 gccaccatgtagcccgcgtcaccgttctgcgcattccgcagc ATG GCT CTG CCT GCC CGA ATC CTC GCT
  1                                            M   A   L   P   A   R   I   L   A

 70 CTG GCC CTC GCA CTG GCG CTC GGA CCC GCC GTG ACA CTG GCC AAC CCG GCG AGA ACG CCG
 10 L   A   L   A   L   A   L   G   P   A   V   T   L   A   N   P   A   R   T   P

130 TAC GAG CTG GTA CTC CAG AAG AGC TCG GCA CGA GGG GGT CGG GAC CAA GGC CCA AAT GTC
 30 Y   E   L   V   L   Q   K   S   S   A   R   G   G   R   D   Q   G   P   N   V

190 TGT GCC CTT CAA CAG ATT TTG GGC ACC AAA AAG AAA TAC TTC AGC ACT TGT AAG AAC TGG
 50 C   A   L   Q   Q   I   L   G   T   K   K   K   Y   F   S   T   C   K   N   W

250 TAT AAA AAG TCC ATC TGT GGA CAG AAA ACG ACT GTG TTA TAT GAA TGT TGC CCT GGT TAT
 70 Y   K   K   S   I   C   G   Q   K   T   T   V   L   Y   E   C   C   P   G   Y

310 ATG AGA ATG GAA GGA ATG AAA GGC TGC CCA GCA GTT TTG CCC ATT GAC CAT GTT TAT GGC
 90 M   R   M   E   G   M   K   G   C   P   A   V   L   P   I   D   H   V   Y   G

370 ACT CTG GGC ATC GTG GGA GCC ACC ACA ACG CAG CGC TAT TCT GAC GCC TCA AAA CTG AGG
110 T   L   G   I   V   G   A   T   T   T   Q   R   Y   S   D   A   S   K   L   R

430 GAG GAG ATC GAG GGA AAG GGA TCC TTC ACT TAC TTT GCA CCG AGT AAT GAG GCT TGG GAC
130 E   E   I   E   G   K   G   S   F   T   Y   F   A   P   S   N   E   A   W   D

490 AAC TTG GAT TCT GAT ATC CGT AGA GGT TTG GAG AGC AAC GTG AAT GTT GAA TTA CTG AAT
150 N   L   D   S   D   I   R   R   G   L   E   S   N   V   N   V   E   L   L   N

550 GCT TTA CAT AGT CAC ATG ATT AAT AAG AGA ATG TTG ACC AAG GAC TTA AAA AAT GGC ATG
170 A   L   H   S   H   M   I   N   K   R   M   L   T   K   D   L   K   N   G   M
```

FIG. 4A

```
 610 ATT ATT CCT TCA ATG TAT AAC AAT TTG GGG CTT TTC ATT AAC CAT TAT CCT AAT GGG GTT
 190 I   I   P   S   M   Y   N   N   L   G   L   F   I   N   H   Y   P   N   G   V

 670 GTC ACT GTT AAT TGT GCT CGA ATC ATC CAT GGG AAC CAG ATT GCA ACA AAT GGT GTT GTC
 210 V   T   V   N   C   A   R   I   I   H   G   N   Q   I   A   T   N   G   V   V

 730 CAT GTC ATT GAC CGT GTG CTT ACA CAA ATT GGT ACC TCA ATT CAA GAC TTC ATT GAA GCA
 230 H   V   I   D   R   V   L   T   Q   I   G   T   S   I   Q   D   F   I   E   A

 790 GAA GAT GAC CTT TCA TCT TTT AGA GCA GCT GCC ATC ACA TCG GAC ATA TTG GAG GCC CTT
 250 E   D   D   L   S   S   F   R   A   A   A   I   T   S   D   I   L   E   A   L

 850 GGA AGA GAC GGT CAC TTC ACA CTC TTT GCT CCC ACC AAT GAG GCT TTT GAG AAA CTT CCA
 270 G   R   D   G   H   F   T   L   F   A   P   T   N   E   A   F   E   K   L   P

 910 CGA GGT GTC CTA GAA AGG ATC ATG GGA GAC AAA GTG GCT TCC GAA GCT CTT ATG AAG TAC
 290 R   G   V   L   E   R   I   M   G   D   K   V   A   S   E   A   L   M   K   Y

 970 CAC ATC TTA AAT ACT CTC CAG TGT TCT GAG TCT ATT ATG GGA GGA GCA GTC TTT GAG ACG
 310 H   I   L   N   T   L   Q   C   S   E   S   I   M   G   G   A   V   F   E   T

1030 CTG GAA GGA AAT ACA ATT GAG ATA GGA TGT GAC GGT GAC AGT ATA ACA GTA AAT GGA ATC
 330 L   E   G   N   T   I   E   I   G   C   D   G   D   S   I   T   V   N   G   I

1090 AAA ATG GTG AAC AAA AAG GAT ATT GTG ACA AAT AAT GGT GTG ATC CAT TTG ATT GAT CAG
 350 K   M   V   N   K   K   D   I   V   T   N   N   G   V   I   H   L   I   D   Q

1150 GTC CTA ATT CCT GAT TCT GCC AAA CAA GTT ATT GAG CTG GCT GGA AAA CAG CAA ACC ACC
 370 V   L   I   P   D   S   A   K   Q   V   I   E   L   A   G   K   Q   Q   T   T

1210 TTC ACG GAT CTT GTG GCC CAA TTA GGC TTG GCA TCT GCT CTG AGG CCA GAT GGA GAA TAC
 390 F   T   D   L   V   A   Q   L   G   L   A   S   A   L   R   P   D   G   E   Y

1270 ACT TTG CTG GCA CCT GTG AAT AAT GCA TTT TCT GAT GAT ACT CTC AGC ATG GAT CAG CGC
 410 T   L   L   A   P   V   N   N   A   F   S   D   D   T   L   S   M   D   Q   R
```

FIG. 4B

1330 CTC CTT AAA TTA ATT CTG CAG AAT CAC ATA TTG AAA GTA AAA GTT GGC CTT AAT GAG CTT

430 L L K L I L Q N H I L K V K V G L N E L

1390 TAC AAC GGG CAA ATA CTG GAA ACC ATC GGA GGC AAA CAG CTC AGA GTC TTC GTA TAT CGT

450 Y N G Q I L E T I G G K Q L R V F V Y R

1450 ACA GCT GTC TGC ATT GAA AAT TCA TGC ATG GAG AAA GGG AGT AAG CAA GGG AGA AAC GGT

470 T A V C I E N S C M E K G S K Q G R N G

1510 GCG ATT CAC ATA TTC CGC GAG ATC ATC AAG CCA GCA GAG AAA TCC CTC CAT GAA AAG TTA

490 A I H I F R E I I K P A E K S L H E K L

1570 AAA CAA GAT AAG CGC TTT ACG ACC TTC CTC AGC CTA CTT GAA GCT GCA GAC TTG AAA GAG

510 K Q D K R F T T F L S L L E A A D L K E

1630 CTC CTG ACA CAA CCT GGA GAC TGG ACA TTA TTT GTG CCA ACC AAT GAT GCT TTT AAG GGA

530 L L T Q P G D W T L F V P T N D A F K G

1690 ATG ACT AGT GAA GAA AAA GAA ATT CTG ATA CGG GAC AAA AAT GCT CTT CAA AAC ATC ATT

550 M T S E E K E I L I R D K N A L Q N I I

1750 CTT TAT CAC CTG ACA CCA GGA GTT TTC ATT GGA AAA GGA TTT GAA CCT GGT GTT ACT AAC

570 L Y H L T P G V F I G K G F E P G V T N

1810 ATT TTA AAG ACC ACA CAA GGA AGC AAA ATC TTT CTG AAA GAA GTA AAT GAT ACA CTT CTG

590 I L K T T Q G S K I F L K E V N D T L L

1870 GTG AAT GAA TTG AAA TCA AAA GAA TCT GAC ATC ATG ACA ACA AAT GGT GTA ATT CAT GTT

610 V N E L K S K E S D I M T T N G V I H V

1930 GTA GAT AAA CTC CTC TAT CCA GCA GAC ACA CCT GTT GGA AAT GAT CAA CTG CTG GAA ATA

630 V D K L L Y P A D T P V G N D Q L L E I

1990 CTT AAT AAA TTA ATC AAA TAC ATC CAA ATT AAG TTT GTT CGT GGT AGC ACC TTC AAA GAA

```
2050 ATC CCC GTG ACT GTC TAT AGA CCC ACA CTA ACA AAA GTC AAA ATT GAA GGT GAA CCT GAA
 670 I   P   V   T   V   Y   R   P   T   L   T   K   V   K   I   E   G   E   P   E

2110 TTC AGA CTG ATT AAA GAA GGT GAA ACA ATA ACT GAA GTG ATC CAT GGA GAG CCA ATT ATT
 690 F   R   L   I   K   E   G   E   T   I   T   E   V   I   H   G   E   P   I   I

2170 AAA AAA TAC ACC AAA ATC ATT GAT GGA GTG CCT GTG GAA ATA ACT GAA AAA GAG ACA CGA
 710 K   K   Y   T   K   I   I   D   G   V   P   V   E   I   T   E   K   E   T   R

2230 GAA GAA CGA ATC ATT ACA GGT CCT GAA ATA AAA TAC ACT AGG ATT TCT ACT GGA GGT GGA
 730 E   E   R   I   I   T   G   P   E   I   K   Y   T   R   I   S   T   G   G   G

2290 GAA ACA GAA GAA ACT CTG AAG AAA TTG TTA CAA GAA GAC ACA CCC GTG AGG AAG TTG CAA
 750 E   T   E   E   T   L   K   K   L   L   Q   E   D   T   P   V   R   K   L   Q

2350 GCC AAC AAA AAA AGT TCA AGG ATC TAG aagacgattaagggaaggtcgttctcagtgaaaatccaaaaacc
 770 A   N   K   K   S   S   R   I   *

2421 agaaaaaaatgtttatacaaccctaagtcaataacctgaccttagaaaattgtgagagccaagttgacttcaggaactga

2501 aacatcagcacaaagaagcaatcatcaaataattctgaacacaaatttaatattttttttttctgaatgagaaacatgagg

2581 gaaattgtggagttagcctcctgtggtaaaggaattgaagaaaatataacaccttacaccctttttcatcttgacattaa

2661 aagttctggctaactttggaatccattagagaaaaatccttgtcaccagattcattacaattcaaatcgaagagttgtga

2741 actgttatcccattgaaaagaccgagccttgtatgtatgttatggatacataaaatgcacgcaagccattatctctccat

2821 gggaagctaagttataaaaataggtgcttggtgtacaaaactttttatgatcaaaaggctttgcacatttctatatgagt

2901 gggtttactggtaaattatgttatttttacaactaattttgtactctcagaatgtttgtcatatgcttcttgcaatgca

2981 tatttttaatctcaaacgtttcAATAAAaccattttcagatataaagagaattacttcaaattgagtaattcagaaaa

3061 actcaagatttaagttaaaaagtggtttggacttgggaataggactttatacctctttctcgtgcc
```

FIG. 4D

Figure 5:
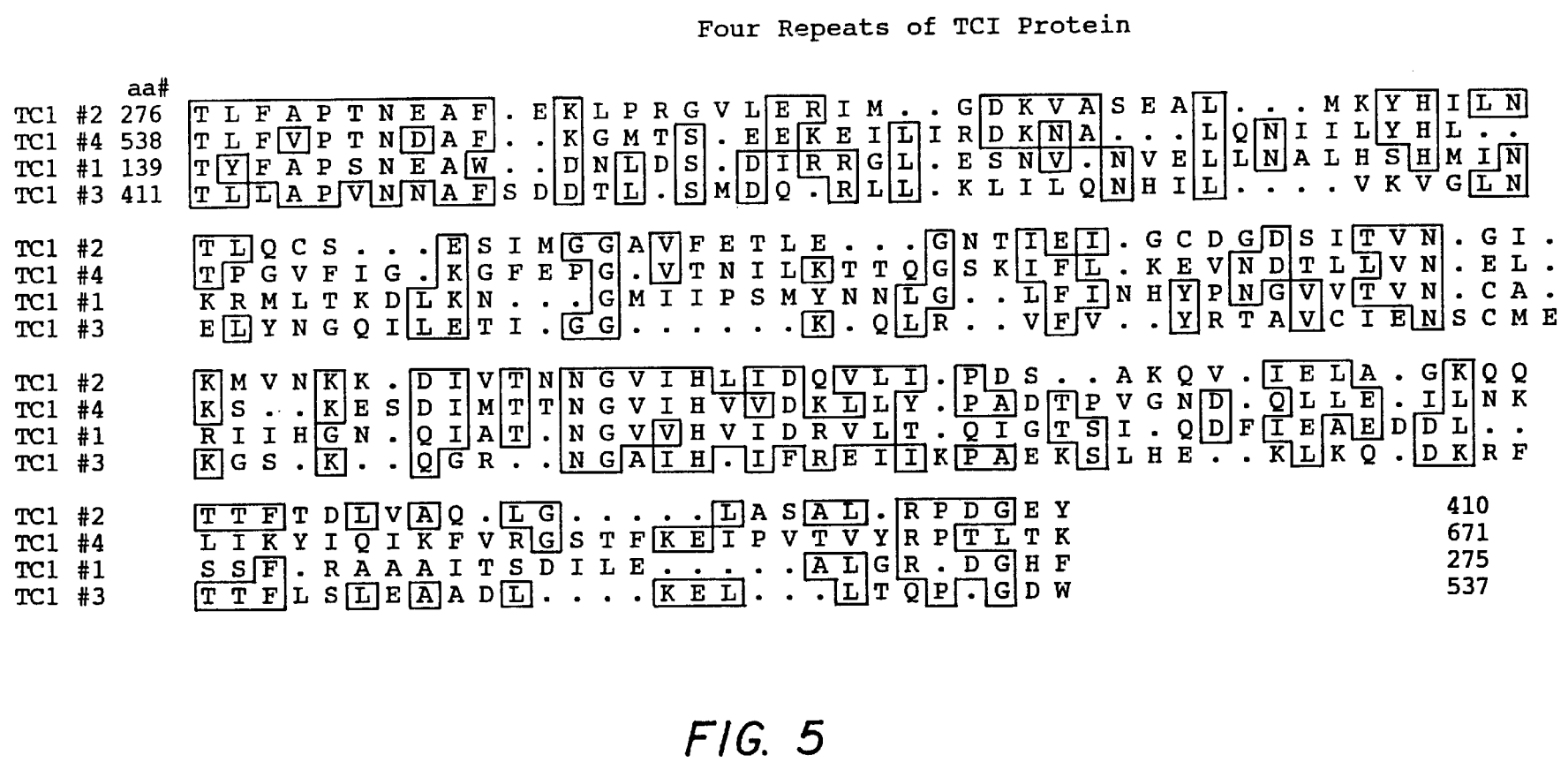

Four Repeats of TCI Protein

```
       aa#
TC1 #2 276  T L F A P T N E A F . E K L P R G V L E R I M . . G D K V A S E A L . . . M K Y H I L N
TC1 #4 538  T L F V P T N D A F . . K G M T S . E E K E I L I R D K N A . . . L Q N I I L Y H L . .
TC1 #1 139  T Y F A P S N E A W . . D N L D S . D I R R G L . E S N V . N V E L L N A L H S H M I N
TC1 #3 411  T L L A P V N N A F S D D T L . S M D Q . R L L . K L I L Q N H I L . . . . V K V G L N

TC1 #2      T L Q C S . . . E S I M G G A V F E T L E . . . G N T I E I . G C D G D S I T V N . G I .
TC1 #4      T P G V F I G . K G F E P G . V T N I L K T T Q G S K I F L . K E V N D T L L V N . E L .
TC1 #1      K R M L T K D L K N . . . G M I I P S M Y N N L G . . L F I N H Y P N G V V T V N . C A .
TC1 #3      E L Y N G Q I L E T I . G G . . . . . . K . Q L R . . V F V . . Y R T A V C I E N S C M E

TC1 #2      K M V N K K . D I V T N N G V I H L I D Q V L I . P D S . . A K Q V . I E L A . G K Q Q
TC1 #4      K S . . K E S D I M T T N G V I H V V D K L L Y . P A D T P V G N D . Q L L E . I L N K
TC1 #1      R I I H G N . Q I A T . N G V V H V I D R V L T . Q I G T S I . Q D F I E A E D D L . .
TC1 #3      K G S . K . . Q G R . . N G A I H . I F R E I I K P A E K S L H E . . K L K Q . D K R F

TC1 #2      T T F T D L V A Q . L G . . . . . L A S A L . R P D G E Y              410
TC1 #4      L I K Y I Q I K F V R G S T F K E I P V T V Y R P T L T K              671
TC1 #1      S S F . R A A A I T S D I L E . . . . . A L G R . D G H F              275
TC1 #3      T T F L S L E A A D L . . . . K E L . . . L T Q P . G D W              537
```

Homology Between TC1 and Bigh3

```
TC1    1  M A L P A R I L A L A L A L A L P P A V T L A N P A R T P Y E L
Bigh3  1  M A L F V R L L A L A L A L A L G P A A T L A G P A K S P Y Q L

          V L Q K S S A R G G R D Q G P N V C A L Q Q I L G T K K K Y F S
          V L Q H S R L R G . R Q H G P N V C A V T K V I G T N R K Y F T

          T C K N W Y K K S I C G Q K T T V L Y E C C P G Y M R M E G M K
          N C K Q W Y Q R K I C G K S T V I S Y E C C P G Y E K V P G E K

          G C P A V L P I D H V Y G T L G I V G A T T T Q R Y S D A S . K
          G C P A A L P L S N L Y E T L G V V G S T T T Q L Y T D R T E K

          L R E E I E G K G S F T Y F A P S N E A W D N L D S D I R R G L
          L R P E M E G P G S F T I F A P S N E A W A S L P A E V L D S L

          E S N V N V E L L N A L H S H M I N K R M L T K D L K N G M I I
          V S N V N I E L L N A L R Y H M V G R R V L T D E L K H G M T L

          P S M Y N N L G L F I N H Y P N G V V T V N C A R I I H G N Q I
          T S M Y Q N S N I Q I H H Y P N G I V T V N C A R L L K A D H H

          A T N G V V H V I D R V L T Q I G T S I Q D F I E A E D D L S S
          A T N G V V H L I D K V I S T I T N N I Q Q I I E I E D T F E T

          F R A A A I T S D I L E A L G R D G H F T L F A P T N E A F E K
          L R A A V A A S G L N T M L E G N G Q Y T L L A P T N E A F E K

          L P R G V L E R I M G D K V A S E A L M K Y H I L N T L Q C S E
          I P S E T L N R I L G D P E A L R D L L N N H I L K S A M C A E

          S I M G G A V F E T L E G N T I E I G C D G D S I T V N G I K M
          A I V A G L S V E T L E G T T L E V G C S G D M L T I N G K A I

          V N K K D I V T N N G V I H L I D Q V L I P D S A K Q V I E L A
          I S N K D I L A T N G V I H Y I D E L L I P D S A K T L F E L A

          G K Q Q T . T F T D L V A Q L G L A S A L R P D G E Y T L L A P
          A E S D V S T A I D L F R Q A G L G N H L S G S E R L T L L A P

          V N N A F S D D T L S M D Q R L L K L I L Q N H I L K V K V G L
          L N S V F K D G T P P I D A H T R N L . L R N H I I K D Q L A S

          N E L Y N G Q I L E T I G G K Q L R V F V Y R T A V C I E N S C
          K Y L Y H G Q T L E T L G G K K L R V F V Y R N S L C I E N S C

          M E K G S K Q G R N G A I H I F R E I I K P A E K S L H E K L K
          I A A H D K R G R Y G T L F T M D R V L T P P M G T V M D V L K

          Q D K R F T T F L S L L E A A D . . . . L K E L L T Q P G D W T
          G D N R F . . . . S M L V A A I Q S A G L T E T L N R E G V Y T
```

```
L F V P T N D A F K G M T S E E K E I L I R D K N A L Q N I I L
V F A P T N E A F R A L P P R E R S R L L G D A K E L A N I L K

Y H L T P G V F I G K G F E P G V T N I L K T T Q G S K I F L K
Y H I . . G D E I L V S G G I G A L V R L K S L Q G D K . . L .

E V . . . N D T L L V N E L K S K E S D I M T T N G V I H V V D
E V S L K N N V V S V N K E P V A E P D I M A T N G V V H V I T

K L L Y P . A D T P . V G N D Q L . . . . L E I L N K L I K Y I
N V L Q P P A N R P Q E R G D E L A D S A L E I . . . . . . . .

Q I K F V R G S T F K E I P V T V Y R P T L T K V K I E G E P E
. . . F K Q A S A F S . . . . . . . R A S Q R S V . . . . . . .

F R L I K E G E T I T E V I H G E P I I K K Y T K I I D G V P V
. R L A . . . . . . . . . . . . . . . . . . . . . . . . . V P Y

E I T E K E T R E E R I I T G P E I K Y T R I S T G G G E T E E
. . . . . . . . . . . . . . . . . . . . . . . . . . . . . . . .

T L K K L L Q E D T P V R K L Q A N K K S S R I          777
. . Q K L L . E . . . . R M . . . . K H . . . .          683
```

Homology Between TC1 and Fasciclin I

```
TC1 503 A E K S L H E K L K Q D K R F T T F L S L L E A A D L
GrF  26 G E K S L E Y K I R D D P D L S Q F Y S W L E H N E V
DrF  19 A A A D L A D K L R D D S E L S Q F Y S L L E S N Q I

TC1     K E L L T Q P G D W T L F V P T N D A F . . . K G M T
GrF     A N S T L Q L R Q V T V F A P T N L A F Q N Y K A R D
DrF     A N S T L S L R S C T I F V P T N E A F Q R Y K . . .

TC1     S E E K E I L I R D K N A L Q N I I L Y H L T P G V F
GrF     G D E N I I L Y H M T N L A H S . . L D Q L G H K V L
DrF     S K T A H V L Y H I T T E A Y T . . Q K R L P N T V S

TC1     I G K . G F E P G V T N I L K T T Q G . S K I F L K E
GrF     S E L D G N P P . . . . . L W I T R R R D T I F . . .
DrF     S D M A G N P P . . L Y I T K N S N G . . D I F . . .

TC1     V N D . T L L V N E L K S K E S D I M . T T N G V I H
GrF     V N N A R V L T . E R S N Y E A V N R H G K K Q V L H
DrF     V G N A R I I P . S L S V . E T N S D . G K R Q I M H

TC1     V V D K L L Y P A D . T P . V G . . . N D Q L L E I L
GrF     V V D S V L E P V W S T S . . G Q L Y N P D A F Q F L
DrF     I I D E V L E P L . . T V K A G H S D T P N N P . . .

TC1     N K L I K Y I Q I K F V R G S T F K E I P V T V Y R P
GrF     N Q . S E N L D L G L H R V R S F R Q R . V F Q . N Q
DrF     N A L . K F . . L K N A E E F N V D N I G V R T Y R S

TC1     T L T K V K I E G E P E F R L I K E G E T I T E V I H
GrF     K Q N D F K L E G K H T F . F I P V D E G F K P L P R
DrF     Q V T M A K K E S V V Y D A A G Q H T F L V P V D E G F

TC1     G E P I I K K                                     706
GrF     P E K I D Q K                                     221
DrF     K L S A R S S                                     211
```

FIG. 9

1, HT29 CELL 3, HT29 TUMOR
2, CX-1 CELL 4, CX-1 TUMOR

1, JMN; 2, JMN1B

1, JMN; 2, JMN1B

NUCLEIC ACIDS ENCODING TUMOR MARKER

This application is a continuation of application Ser. No. 08/348,747, filed Dec. 1, 1994, which was a continuation of application Ser. No. 08/146,4888, Oct. 29, 1993 (both now abandoned).

GOVERNMENT RIGHTS

This invention was made part with U.S. Government support. Therefore, the U.S. Government has certain rights in the invention.

FIELD OF THE INVENTION

The invention relates to proteins that serve as tumor markers for human carcinoma and to methods of isolating differentially expressed genes.

BACKGROUND OF THE INVENTION

Tumor markers for human tumor cells have been largely limited to activated oncogenes and their products, for example, the myc, ras, fos, and erbB2 genes and their encoded oncoproteins. In addition, activated anti-oncogenes, such as RB, p53, and DCC, have been identified in normal cells but do not appear to be present in tumor cells. Oncogene and anti-oncogene products have proven difficult to use as consistent predictors of tumor and normal tissue, respectively, due to the relatively low level of expression of the genes encoding these proteins. Thus, there is a need in the art for a tumor marker which is not only differentially expressed in tumor and normal tissue, but also consistently detectable in human tumor tissue and consistently absent in the corresponding normal tissue.

A common method used to identify genes differentially or uniquely expressed in tumors, in cells responding to growth factors, and in differentiated cell types such as, among others, T cells, adipocytes, neurons, and hepatocytes is the subtractive hybridization technique (S. W. Lee et al., Proc. Natl. Acad. Sci. USA 80:4699, 1983). A method of differential display of eukaryotic mRNA by means of the polymerase chain reaction (PCR) has recently been developed (P. Liang et al., Science 257:967, 1992). This method utilizes oligo dT linked to two additional bases as the primer for reverse transcription driven by reverse transcriptase. cDNA fragments are then amplified by Taq DNA polymerase-based PCR using an oligo dT primer along with one additional primer. The amplified cDNAs are then resolved by DNA sequencing gels. There is a need in the art for a streamlined and simplified process for isolating cDNAs corresponding to differentially expressed mRNAs.

SUMMARY OF THE INVENTION

The invention is based on the discovery of a novel protein, TC1 (SEQ ID NO: 4), which is a tumor marker, particularly for invasive and metastatic tumors, and the gene encoding this protein.

The invention thus encompasses the TC1 protein (SEQ ID NO: 4), which is useful as a tumor marker for tumor diagnosis and therapy, particularly for colorectal, breast, and gastrointestinal tumors, and for metastatic tumors emanating from these tumor types. TC1 is also a useful marker in general for tumor cell invasion and metastasis. mRNA encoding TC1 is not expressed in most cultured tumor cells, i.e., in vitro, but is expressed once these cells are grown in vivo. Because later stage and deeply invasive tumors contain higher levels of TC1 protein than other tumor tissues, TC1 appears to be a particularly useful marker for later stage cancers.

TC1 protein may also serve as a target in tumor targeted therapy to prevent tumor cell metastasis and thus invasion of additional organs. For example, a polypeptide fragment of the TC1 protein may be used as an antagonist of TC1 biological activity; e.g., where TC1 biological activity includes invasion and metastasis, the polypeptide fragment may be administered to a patient afflicted with the tumor in order to inhibit the spread of the tumor to other tissues. Alternatively, a truncated portion of TC1 which retains the invasive and metastatic biological activities of the full-length molecule will be useful for screening for antagonists of TC1 activity. Potentially useful polypeptides are described herein.

The invention also encompasses nucleotide probes based on the TC1 nucleotide sequence; e.g., 10, 20, 30, 40, etc. nucleotides in length. Such probes are useful for PCR-based tumor detection and in situ hybridization of tumor tissue sections. In addition, probes whose nucleotide sequences are based on homologies with other genes or proteins having sequences related to TC1, i.e., genes of the TC1 family, two of which are described herein, are useful for detecting additional genes belonging to the TC1 family of genes.

The invention thus also encompasses methods of screening for agents which inhibit expression of the TC1 gene (SEQ ID NO: 3) in vitro, comprising exposing a metastatic cell line in which TC1 mRNA is detectable in cultured cells to an agent suspected of inhibiting production of the TC1 mRNA; and determining the level of TC1 mRNA in the exposed cell line, wherein a decrease in the level of TC1 MRNA after exposure of the cell line to the agent is indicative of inhibition of TC1 mRNA production.

Alternatively, the screening method may include in vitro screening of a metastatic cell line in which TC1 protein is detectable in cultured cells to an agent suspected of inhibiting production of the TC1 protein; and determining the level of TC1 protein in the cell line, wherein a decrease in the level of TC1 protein after exposure of the cell line to the agent is indicative of inhibition of TC1 protein production.

The invention also encompasses in vivo methods of screening for agents which inhibit expression of the TC1 gene, comprising exposing a mammal having tumor cells in which TC1 mRNA or protein is detectable to an agent suspected of inhibiting production of TC1 mRNA or protein; and determining the level of TC1 mRNA or protein in tumor cells of the exposed mammal. A decrease in the level of TC1 mRNA or protein after exposure of the mammal to the agent is indicative of inhibition of TC1 gene expression.

These screening methods are particularly applicable to breast tumor cells, colon tumor cells, or tumor cells of the gastrointestinal tract.

The invention also encompasses a method of treating late stage cancer, comprising administering to a mammal afflicted with a late stage cancer a therapeutically effective amount of an inhibitor of TC1. Late stage cancers include those which have become deeply invasive in a tissue or which have metastisized to other tissues.

TC1 is detectable in patient blood, urine, sputum or other body fluid using a monoclonal antibody specific for a TC1 epitope. Thus, the invention also encompasses antibodies specific for TC1. Monoclonal antibodies specific for TC1 may be used for tumor imaging to localize tumor position and size. TC1-specific monoclonal antibodies are also useful as screening and diagnostic agents in immunohistochemical staining of tissue sections to distinguish tumor cells from normal cells. Thus, anti-TC1 antibodies are particularly useful where they recognize cells which produce the TC1 protein, when such cells are paraffin-embedded and/or formalin-fixed. One example of such an antibody is the monoclonal antibody anti-TC1-1 produced by the hybridoma deposited with the American Type Culture Collection as ATCC Deposit No. HB 11481.

In another aspect, the invention also features a novel method, called palindromic PCR, for identifying and isolating a gene, e.g., a gene which is differentially expressed in different types of tissues. The method is based on the use of short DNA primers and corresponding palindromic nucleotide sequences in the nucleotide sequence to be isolated.

Thus, the invention encompasses a method for producing a double stranded cDNA that includes the steps of contacting an mRNA with a DNA primer under stringent hybridization conditions to form a first hybrid molecule, the primer having a length of from 8 to 12 nucleotides and, preferably, 9 to 11 nucleotides; subjecting the first hybrid molecule to an enzyme having reverse transcriptase activity, to produce a first DNA strand complementary to at least a portion of the mRNA; contacting the first DNA strand with the primer under stringent hybridization conditions to form a second hybrid molecule; and subjecting the second hybrid molecule to an enzyme having DNA polymerase activity, to produce a second DNA strand complementary to the first DNA strand. Preferably, the method also includes the step of amplifying the first and second DNA strands.

In preferred embodiments, a single enzyme provides both the reverse transcriptase activity and the DNA polymerase activity. One example of a suitable such enzyme is rTth DNA polymerase from the *thermophilic eubacterium Therzmus thermophilus.*

As used herein, the term "palindromic nucleotide sequences" means that a double stranded DNA molecule contains a specific DNA sequence in both its coding strand and its anti-parallel strand, when those strands are read in the same direction, e.g., 5' to 3'.

The specific sequence of the DNA primer is arbitrary in that it is based upon individual judgment. In some instances, the sequence can be entirely random or partly random for one or more bases. Preferably, the GC content of the primer is between 40% and 60%, most preferably about 50%. In other instances, the arbitrary sequence can be selected to contain a specific ratio of each deoxynucleotide. The arbitrary sequence can also be selected to contain, or not to contain, a recognition site for a specific restriction endonuclease.

The DNA primer can contain a sequence that is known to be a "consensus sequence" of an mRNA of known sequence. As defined herein, a "consensus sequence" is a sequence that has been found in a gene family of proteins having a similar function or similar properties. The use of a primer that includes a consensus sequence may result in the cloning of additional members of a desired gene family.

Palindromic PCR enables genes that are altered in their frequency of expression, as well as those that are constitutively or differentially expressed, to be identified by simple visual inspection and isolated. The method also allows the cloning and sequencing of selected mRNAs, so that the investigator may determine the relative desirability of the gene product prior to screening a comprehensive cDNA library for the full length gene product.

Further objects and advantages of the invention will be apparent in light of the following description and the claims.

The file of this patent contains at least one color drawing. Copies of this patent with color drawing(s) will be provided by the Patent and Trademark Office upon request and payment of the necessary fee.

BRIEF DESCRIPTION OF THE DRAWINGS

FIG. 3 shows the nucleotide sequence (described herein as SEQ ID NO: 1) and corresponding amino acid sequence (SEQ ID NO: 2) of the 636 bp partial TC1 clone.

FIG. 4 shows the nucleotide sequence (SEQ ID NO: 3) and corresponding amino acid sequence (SEQ ID NO: 4) of the full-length TC1 gene and protein.

FIG. 5 is a sequence comparison of the four internal homologous domains of TC1 (SEQ ID NO: 4), each approximately 135 amino acids.

FIG. 7 shows the amino acid sequence identity between TC1 (SEQ ID NO: 4) and Big-h3 (SEQ ID NO: 17).

FIG. 9 shows amino acid sequence homology between TC1 (SEQ ID NO: 4) and Fasciclin I from Grasshopper (GrF) (SEQ ID NO: 18) and Drosophila (DrF) (SEQ ID NO: 19).

TGTCCAGCCG) (SEQ ID NO: 10); E', 80% (5'-TGTCCCGCCG) (SEQ ID NO: 11); F', 90% (5'-TGCCCGGCCG) (SEQ ID NO: 12).

Figure 13A:
FIG. 13A shows the effect of the length of the DNA primer on the cDNA amplification patterns; the length and nucleotide sequence of each primer are: A, 8-mer (5'-TGTCGAGA); B', 9-mer (5'-TGTCCAGAC); C', 10-mer (5'-TGTCCAGATG) (SEQ ID NO: 5); D', 11-mer (5'-TGTCCAGATGC) (SEQ ID NO: 6); E', 12-mer (5'-TGTCCAGATGAC) (SEQ ID NO: 7).
Figure 13B:
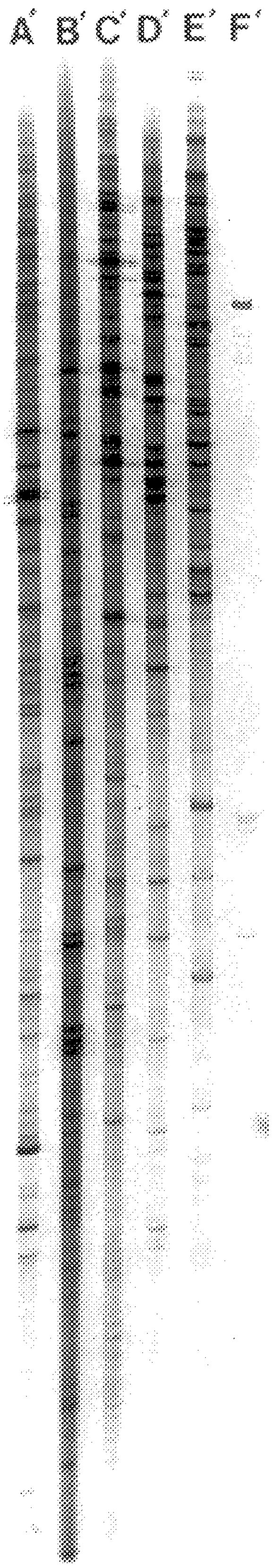
FIG. 13B shows the effect of the GC content of the DNA primer on the cDNA amplification patterns; the GC content and nucleotide sequence of each primer (10-mer) are: A', 40% (5'-TGTCCAGATA) (SEQ ID NO: 8); B', 50% (5'-TGTCCAGATG) (SEQ ID NO: 5); C', 60% (5'-TGTCCAGACG) (SEQ ID NO: 9): D', 70% (5'-
Figure 13C:
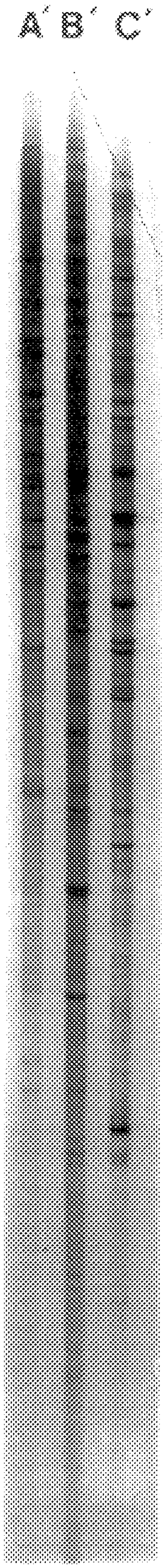

FIG. 13C shows the effect of the sequence specificity of the DNA primer on the cDNA amplification patterns; 10-mer primers with the same GC content but different sequences are: A', 5'-TGATGCACTC (SEQ ID NO: 13); B', 5'-TGAGCTACTC (SEQ ID NO: 14); C', 5'-TGACTGACTC (SEQ ID NO: 15).

Figure 13D:
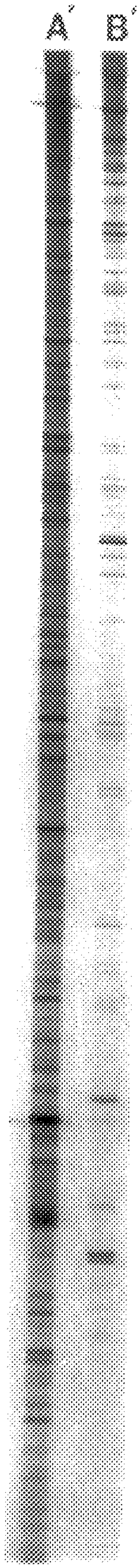

FIG. 13D shows palindromic PCR performed by rTth DNA polymerase (A) with reverse transcription cycles (RT cycles) and (B) without RT cycles.

Figure 14A:
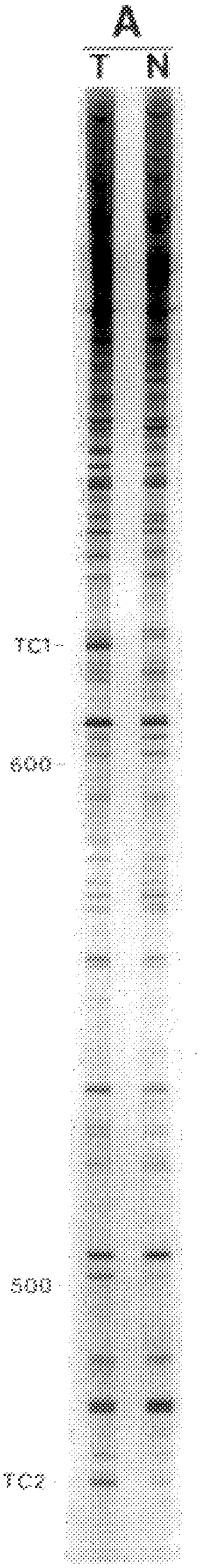
Figure 14B:
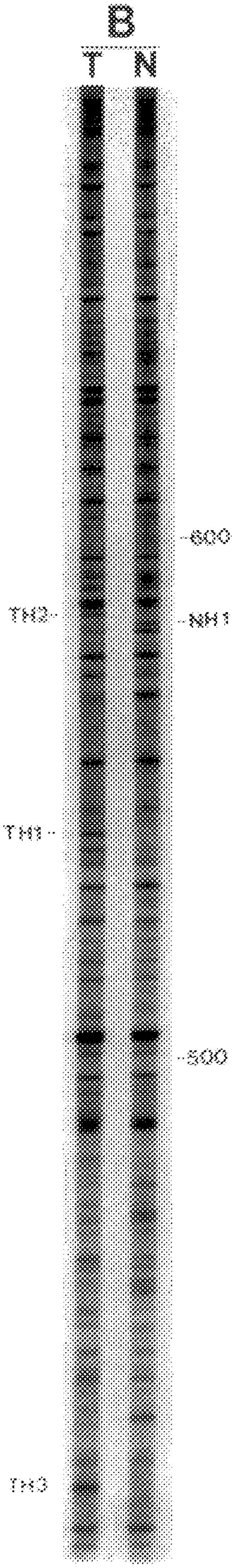

FIG. 14A–14B show the identification of differentially expressed genes in human colon carcinoma.

Figure 15:
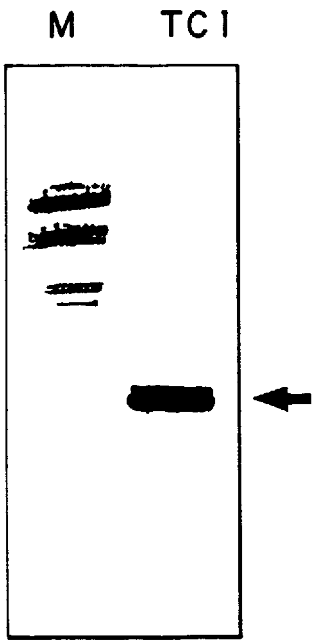

FIG. 15 shows reamplification of the TC1 cDNA fragment isolated from colon carcinoma; the PCR product was analyzed on a 1.0% agarose gel; a 0.63 Kb cDNA fragment (arrow) was detected.

Figure 16A:
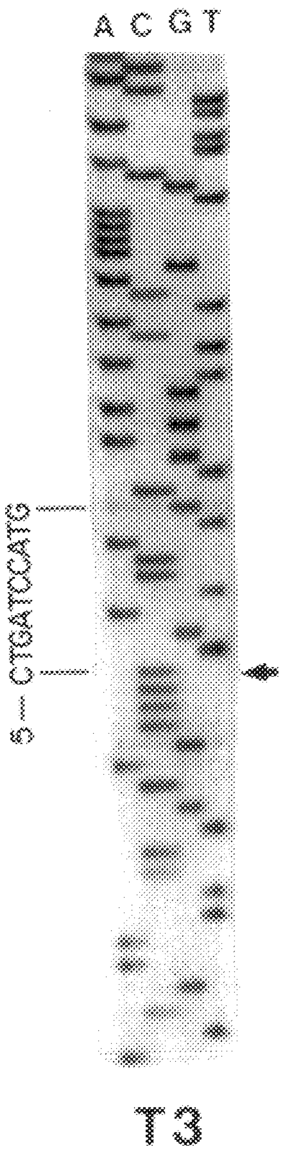
Figure 16B:
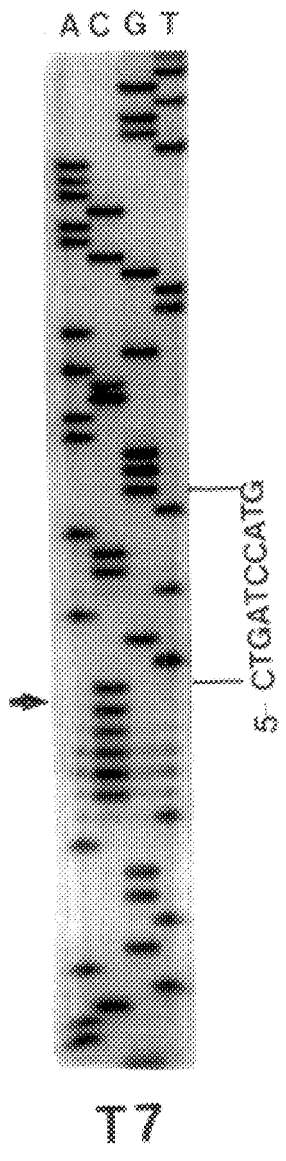

FIG. 16 is an autoradiogram of DNA sequencing gels showing the presence of PP1 primer sequence (5'-CTGATCCATG) (SEQ ID NO: 16) at the 5'-end of both strands of the TC1 cDNA fragment; cloning sites are indicated by arrows, sequences below arrows are pBS (KS) vector sequences reading from T3 primer and T7 primer.

Figure 17A:
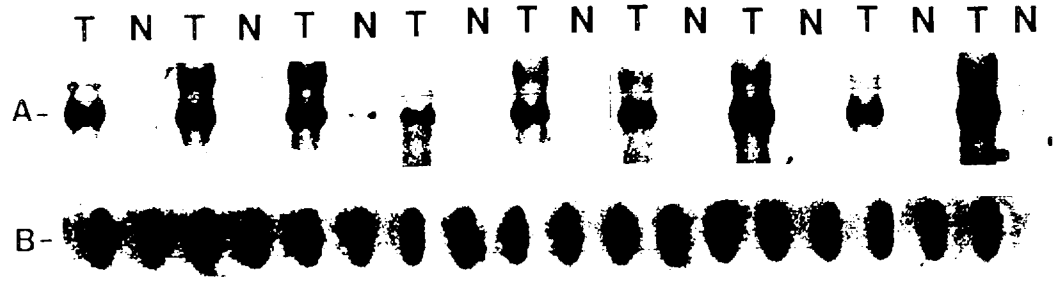
Figure 17B:
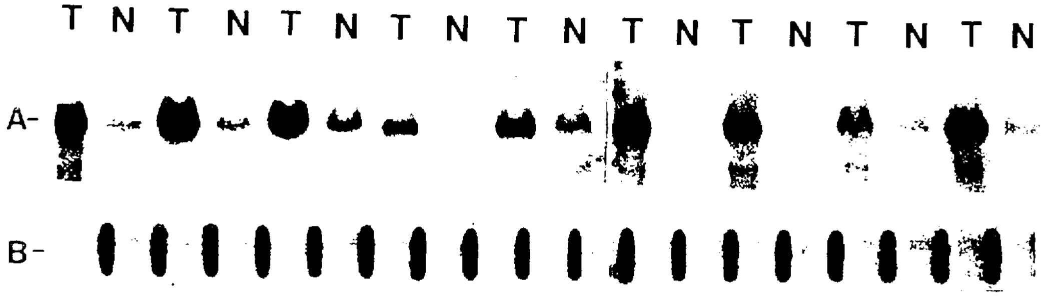
Figure 17C:
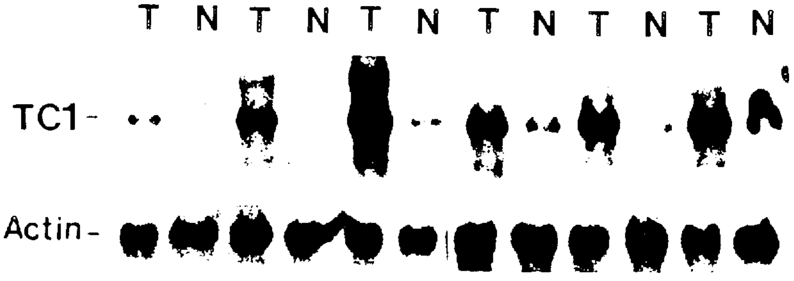

FIG. 17 is a Northern Blot of 24 pairs of colon carcinoma (T) and their adjacent normal tissue (N) probed with 32P-labeled TC1 cDNA.

Figure 18:
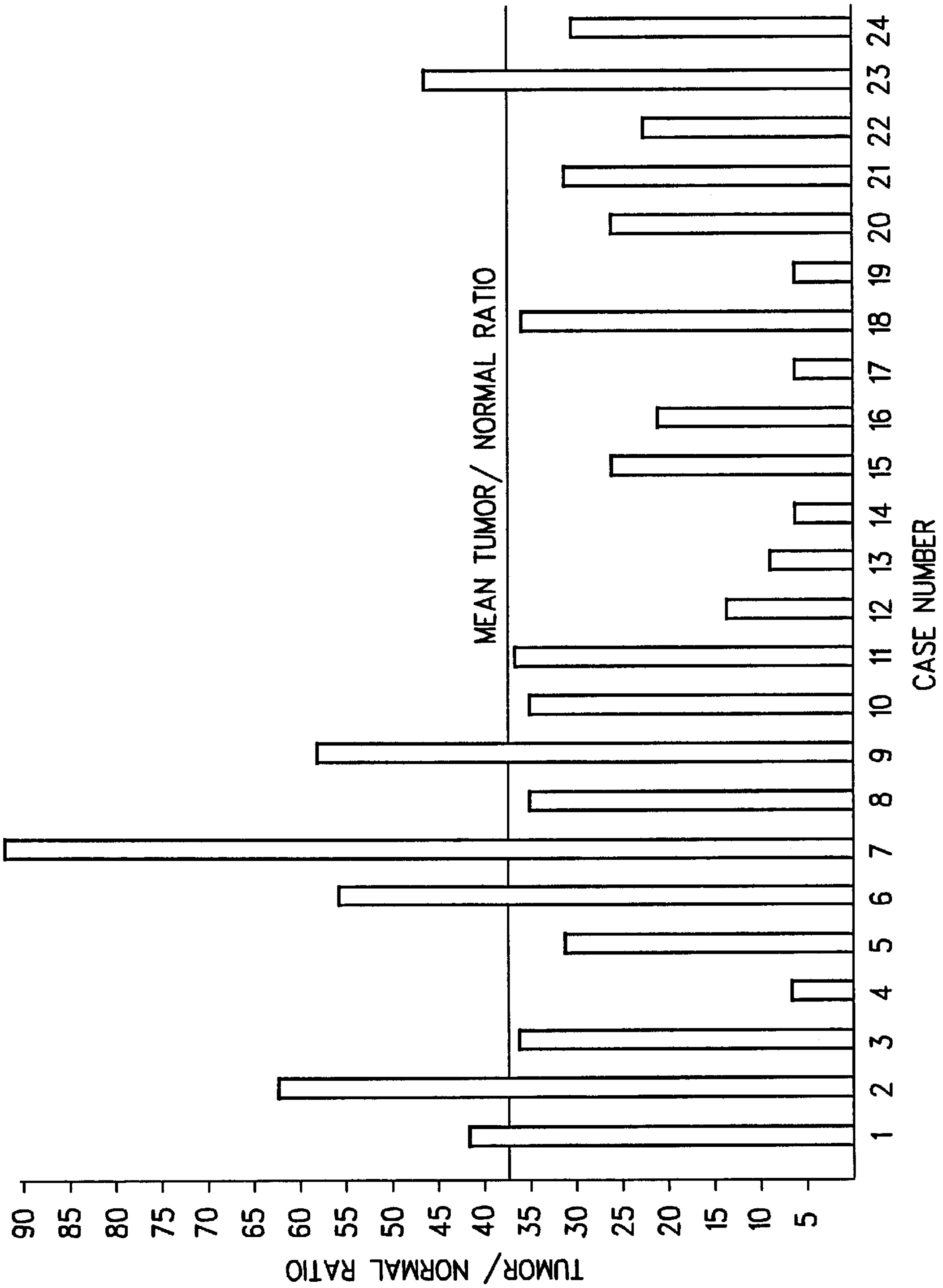

FIG. 18 shows the Tumor/Normal RNA Ratio from Northern Blot results of FIG. 17.

Figure 19:
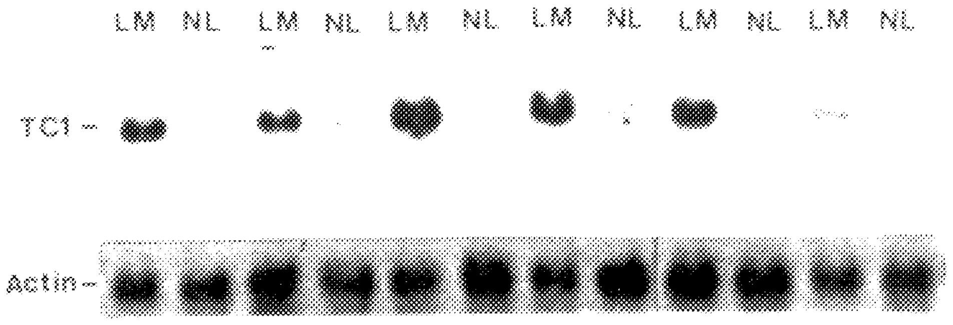

FIG. 19 is a Northern Blot of RNA from carcinoma cells which result from metastasis from colon carcinoma to liver (LM) and their adjacent normal liver (NL) probed with $^{32}$P-labeled TC1 cDNA.

Figure 20:
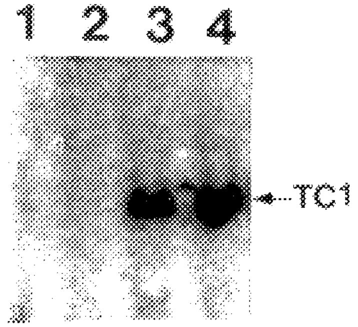

FIG. 20 shows a Northern Blot of RNA from breast cancer cell line MCF-7 (1) and colon cancer cell line CX-1 (2) cultured in vitro, and MCF-7 tumor (3) and CX-1 tumor (4) grown in vivo in nude mice.

FIGS. 21A–21D show staining of formalin-fixed and paraffin-embedded colon tumor tissue sections using the monoclonal antibody anti-TC1-1 and avidin-biotin-peroxidase detection.

FIG. 22 shows staining as described in FIG. 21, except that panels A, C, D represent breast invasive ductal carcinoma and panel B, normal breast tissue.

FIG. 23 shows staining as in FIG. 13, except that panels A and B represent gastric carcinoma, and panels C and D, deeply invasive colon carcinoma.

Figure 24A:
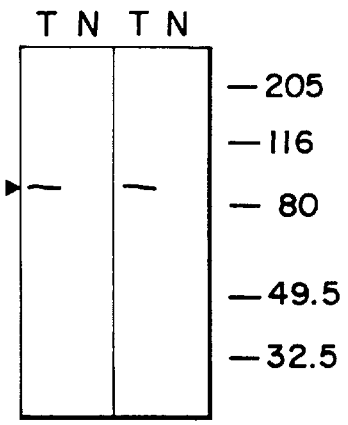
Figure 24B:
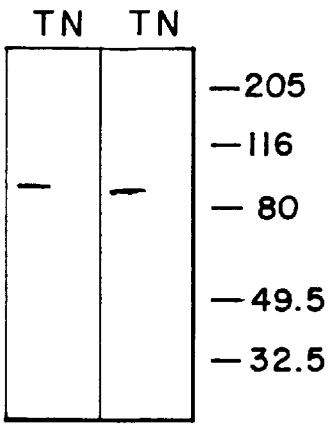

FIG. 24 is a Western Blot analysis of protein samples from two pairs of colon carcinoma and their adjacent normal colon (A) and two pairs of breast carcinoma and their adjacent normal breast (B), using a monoclonal antibody against TC1 protein as a probe.

Figure 25A:

FIG. 25A shows the ethidium bromide staining pattern of an RNA gel in which the same amount of RNA from JMN (1) and JMN1B (2) cells is loaded per lane.

Figure 25B:
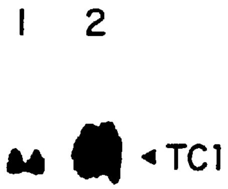

FIG. 25B is a Northern Blot analysis of RNA from malignant mesothelioma cells JMN1B (2) and JMN (1) using TC1 cDNA as a probe.

Figure 26:
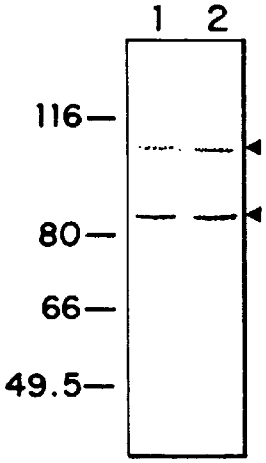
Figure 27A:
Figure 27B:
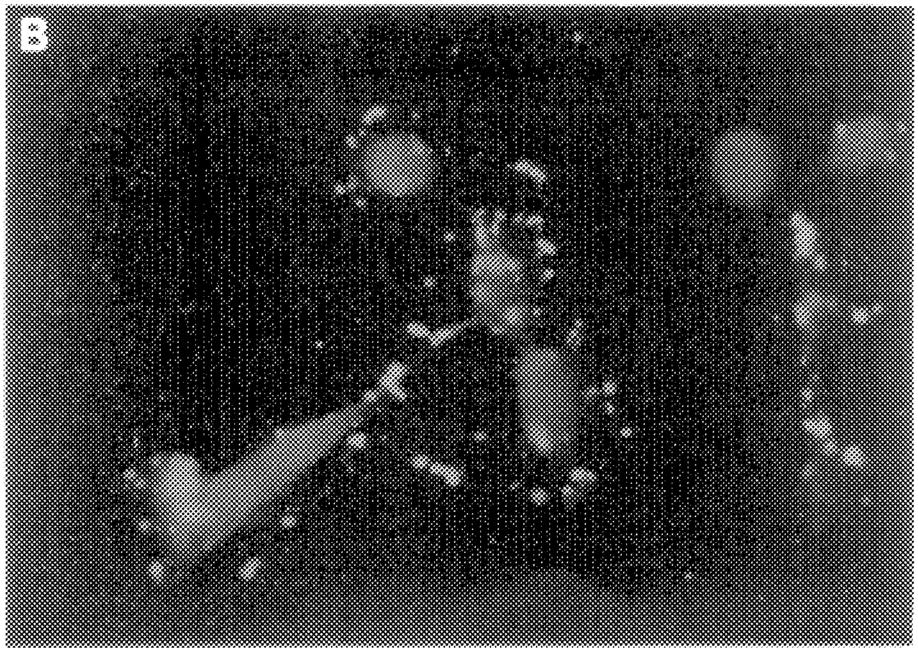
Figure 27C:
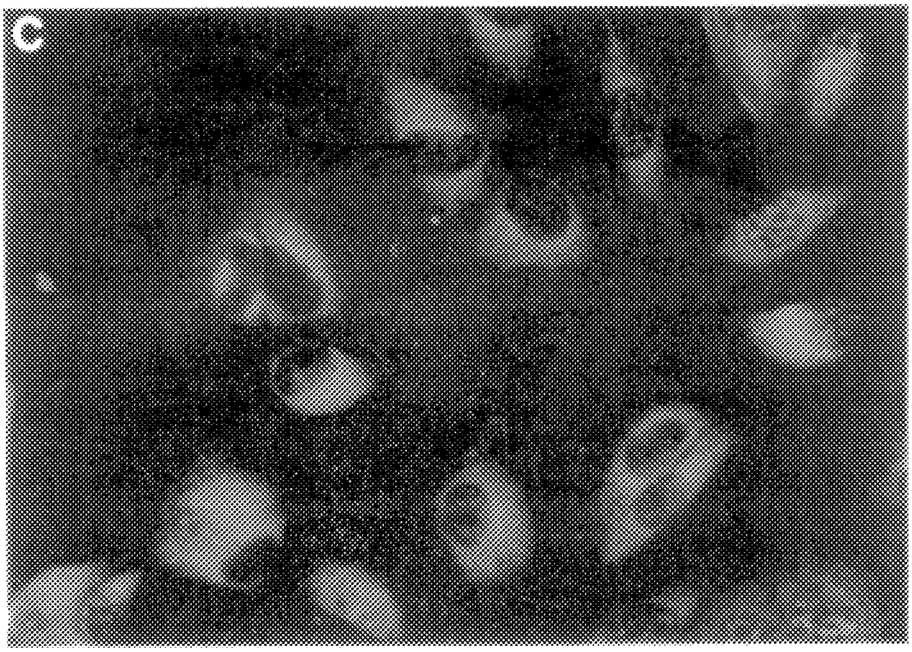
Figure 27D:

FIG. 26 is a Western blot using a monoclonal antibody against TC1 to probe JMN1B cells grown in conditioned medium and whole cell lysate.

FIG. 27 shows JMN1B cells fixed with paraformaldehyde without subsequent permeabilization in panels A and B, and JMN1B cells fixed with paraformaldehyde and then permeabilized in panels C and D.

DESCRIPTION OF THE PREFERRED EMBODIMENTS

TC1 (SEQ ID NO: 4) is a novel protein that is found in invasive and metastatic tumor cells. The nucleotide sequence encoding TC1 (SEQ ID NO: 3) was found using a novel technique described herein as palindromic PCR, a technique which enables identification and cloning of a gene that is differentially expressed in tissues. Cloning and sequencing of the gene encoding TC1 and characterization of the protein is described below, along with examples of how the protein is detected in invasive and metastatic cancers. Examples describing additional uses of the TC1 protein and its fragments, the nucleotide sequence encoding TC1 and fragments thereof, and antibodies specific for TC1 are also included.

Identification, Cloning and Detection of Expression of the TC1 Gene

Figure 1:
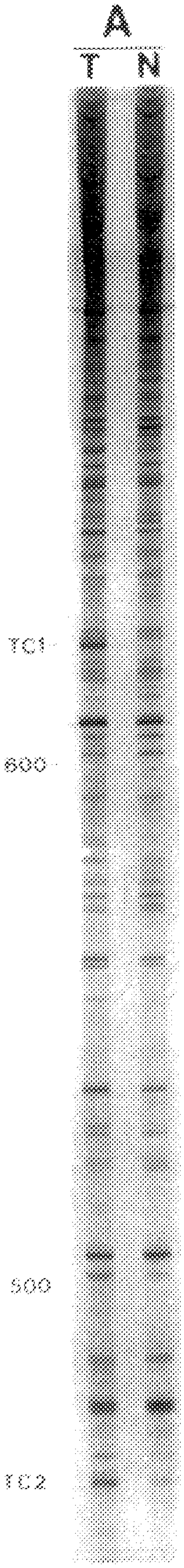
FIG. 1 is a polyacrylamide gel of size-separated cDNAs that were reverse transcribed from paired mRNAs from colon carcinoma (T) and adjacent normal colon tissue (N) and subsequently amplified.
Figure 2A:
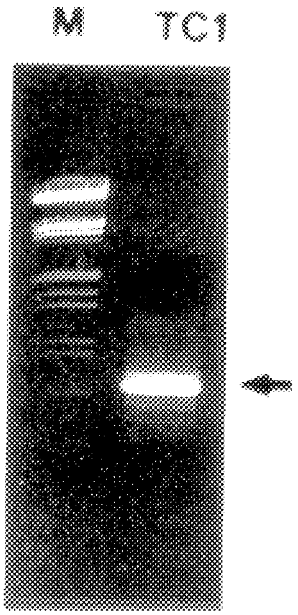
FIG. 2A is a gel in which the TC1 cDNA fragment identified in FIG. 1 was recovered and re-amplified.

The identification, cloning, and differential detection of expression of the TC1 gene (SEQ ID NO: 3) was performed as follows. A 636 bp cDNA fragment (SEQ ID NO: 1) containing TC1 sequences was identified and isolated by a rapid method termed palidromic PCR, described herein, from human surgical colon carcinoma tissue. Briefly, paired mRNAs were isolated from colon carcinoma tissue and adjacent normal colon tissue from the same patient, then matched mRNAs were reverse transcribed to cDNA and subsequently amplified by the palindromic PCR method described herein, which utilizes one DNA primer. Both reverse transcription and PCR reactions were driven by a single enzyme, rTth DNA polymerase, in a single tube. $^{35}$S or $^{33}$P-labeled PCR cDNA fragments were resolved on a DNA sequencing gel. As shown in FIG. 1, paired mRNAs from colon carcinoma (T) and adjacent normal colon tissue (N) were reverse transcribed to cDNA and subsequently amplified by palindromic PCR. $^{35}$S-labeled PCR cDNA fragments were then resolved on a DNA sequencing gel. A differential cDNA band (TC1) appeared to be present only in the tumor sample. This TC1 cDNA fragment was recovered from the sequencing gel and then reamplified with the same palindromic primer. This 636 bp fragment is identified with a horizontal arrow in FIG. 2A.

Figure 2B:
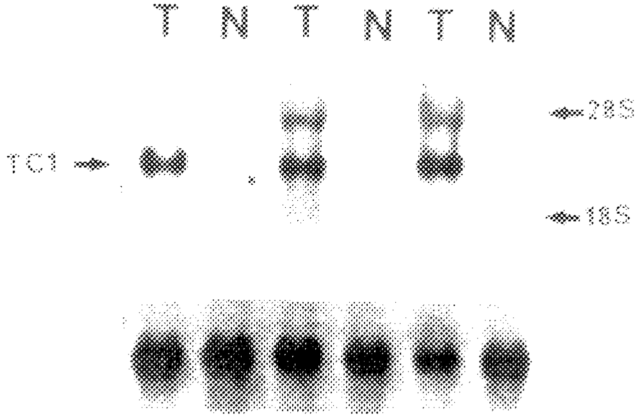
FIG. 2B is a Northern Blot of three pairs of RNA from colon carcinoma (T) and their adjacent normal colon tissue (N) probed with 32P-labeled TC1 cDNA.

TC1 gene expression was examined in colon carcinoma cells and in the corresponding adjacent colon tissue, and the results were as follows. FIG. 2B is a Northern Blot of three pairs of RNA from colon carcinoma (T) and their adjacent normal colon tissue (N) probed with $^{32}$P-labeled TC1 cDNA. TC1 mRNA was over-expressed in all three cases of colon carcinoma, whereas only very weak TC1 message appeared in the adjacent normal tissue. In the bottom panel of the blot, control RNA was blotted with $^{32}$P-labeled cDNA encoding B-actin.

Northern Blot analysis of several pairs of Tumor/Normal total RNA using a 32P-labeled TC1 cDNA probe revealed that the TC1 mRNA size is about 3.6 Kb. This first TC1 cDNA fragment was cloned into a pBluescript plasmid DNA vector strategies. Nucleotide sequence analysis revealed that this fragment contained 636 bp with nucleotide sequences corresponding to the primer sequence at both 5'-ends of the double-stranded DNA (FIG. 3 and SEQ ID NO: 1). The corresponding predicted amino acid sequence is shown in FIG. 3 and provided in SEQ ID NO: 2. A search of the GenBank database with this cDNA fragment revealed that TC1 is a novel gene.

Nucleotide sequence analysis of the 636 bp TC1 cDNA fragment obtained by the described differential display method revealed that it contained a partial open reading frame. Therefore, this 636 bp cDNA fragment was used as probe to screen a cDNA library. Several overlapping clones were obtained and contained a 2997 bp sequence. To obtain the complete open reading frame for TC1, a modified 5'-end RACE technique was used to amplify the TC1 coding regions. The nucleotide and deduced amino acid sequence of full-length TC1 is shown in FIG. 4 and provided in SEQ ID NOS: 3 and 4. The N-terminal signal sequence is underlined; one predicted N-linked glycosylation site (NDT) is boxed and a polyadenylation signal (AATAAA) (SEQ ID NO: 3, nucleotide residues 3004–3009) is indicated. The cDNA contains 3126 bp with a potential polyadenylation sequences (AATAAA) at the 3'-end, beginning at residue 3004 (SEQ ID NO: 3, nucleotide residues 3004–3009). The open reading frame (ORF) encodes a 777-amino acid protein with a calculated molecular weight of 86 kD. The TC1 protein contains an amino-terminal signal peptide or secretory leader signal (ALPARILALALALAL) (SEQ ID NO: 4, amino acid residues 2–16), and one predicted site of N-linked 7 glycosylation at amino acid residue 605 (NDT). One Cemokine B family motif (C—C) was found at amino acid residue 85 (C—C) of TC1.

Figure 6:
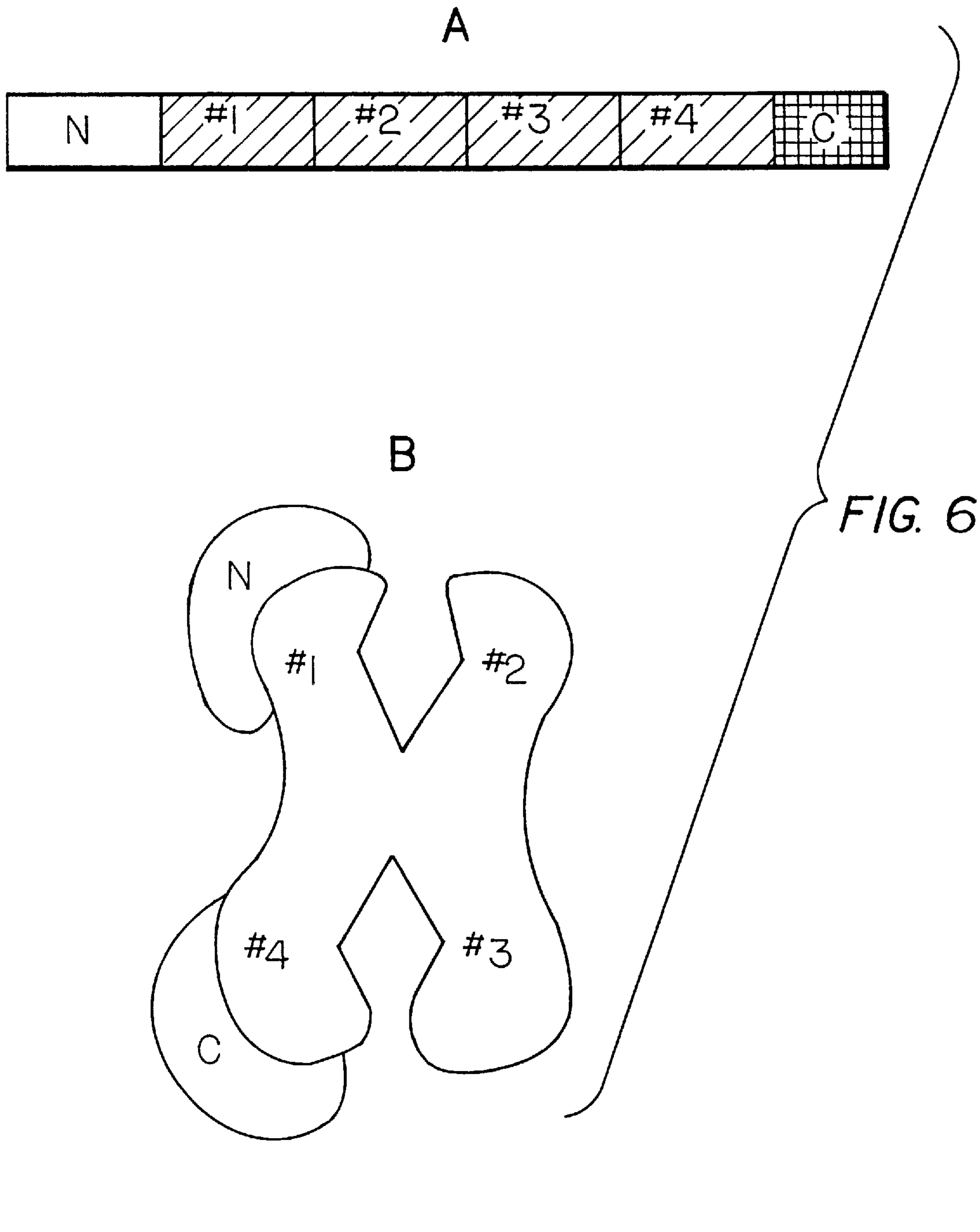
FIG. 6A is a schematic representation of the four repeats of TC1.
FIG. 6B is a proposed schematic arrangement of the four repeated domains and the N- and C-terminal domains.

Analysis of the deduced amino acid sequence (SEQ ID NO: 4) revealed that TC1 contained four internal homologous domains of approximately 135 amino acids. A comparison of these repeats is shown in FIG. 5. Each boxed amino acid is identical with at least one other residue at that same position. The interdomain homologies range from 32% (between domains 2 and 4) to 18% (between domains 1 and 3). Some amino acid sequence such as TLFA/VPT/SNEAF (see SEQ ID NO: 4, amino acid residues 276–285), NGVIHXID (see SEQ ID NO: 4, amino acid residues 361–368) are highly conserved between all four repeats. The notations A/V and T/S are used herein to indicate that alanine or valine, and threonine or serine, respectively, may be found at these positions. In addition, the notation X is used herein to indicate that this position may include any amino acid. Each repeat starts with the most divergent sequence. The four repeats occur between residues 139–537 and are uninterrupted by non-homologous domains. A schematic representation of the four repeats of TC1 is shown in FIG. 6A. The four homologous repeats suggest a tetrameric structure (Mclachlan 1980; Zinn et al, 1988) with two binding sites, one at each intrachain dimer. The four repeats of TC1 may serve as ligand binding sites, with the N-terminal or C-terminal domains serving as the functional domain. One possible arrangement of the four repeated domains and the N- and C-terminal domains is shown schematically in FIG. 6B.

Palindromic PCR

Described below is a novel technique used to identify the TC1 mRNA and prepare TC1 cDNA. Although the sequence of bases in a coding and antisense strand of a cDNA molecule are, in a sense, "mirror images" of one another, we have found that with surprising frequency a short sequence of bases, e.g. 9 or 10, in one strand will be found to have an exact copy in its anti-parallel strand. We call these sequences "palindromic" sequences. This phenomenon has been used to develop a method of cDNA isolation and amplification.

Figure 10:
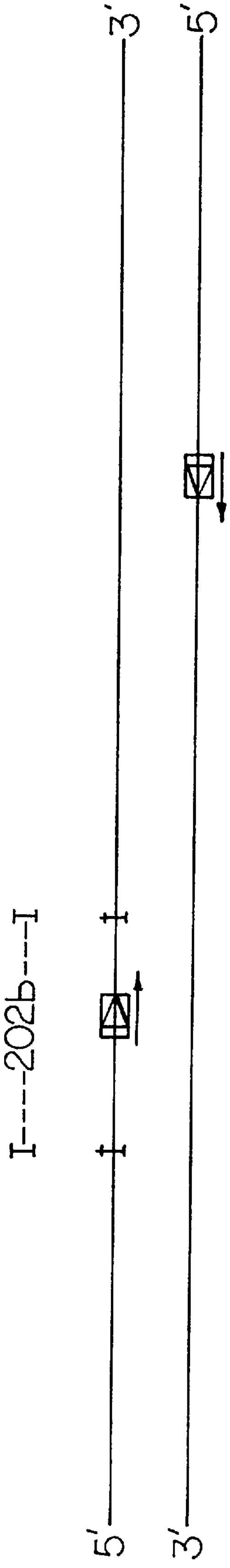
FIG. 10 is a Schematic representation showing that, on average, in every 202 bases of sequence in one strand of cDNA, there is one 9-base sequence exactly palindromic to that in a region of its antiparallel strand.
Figure 11:
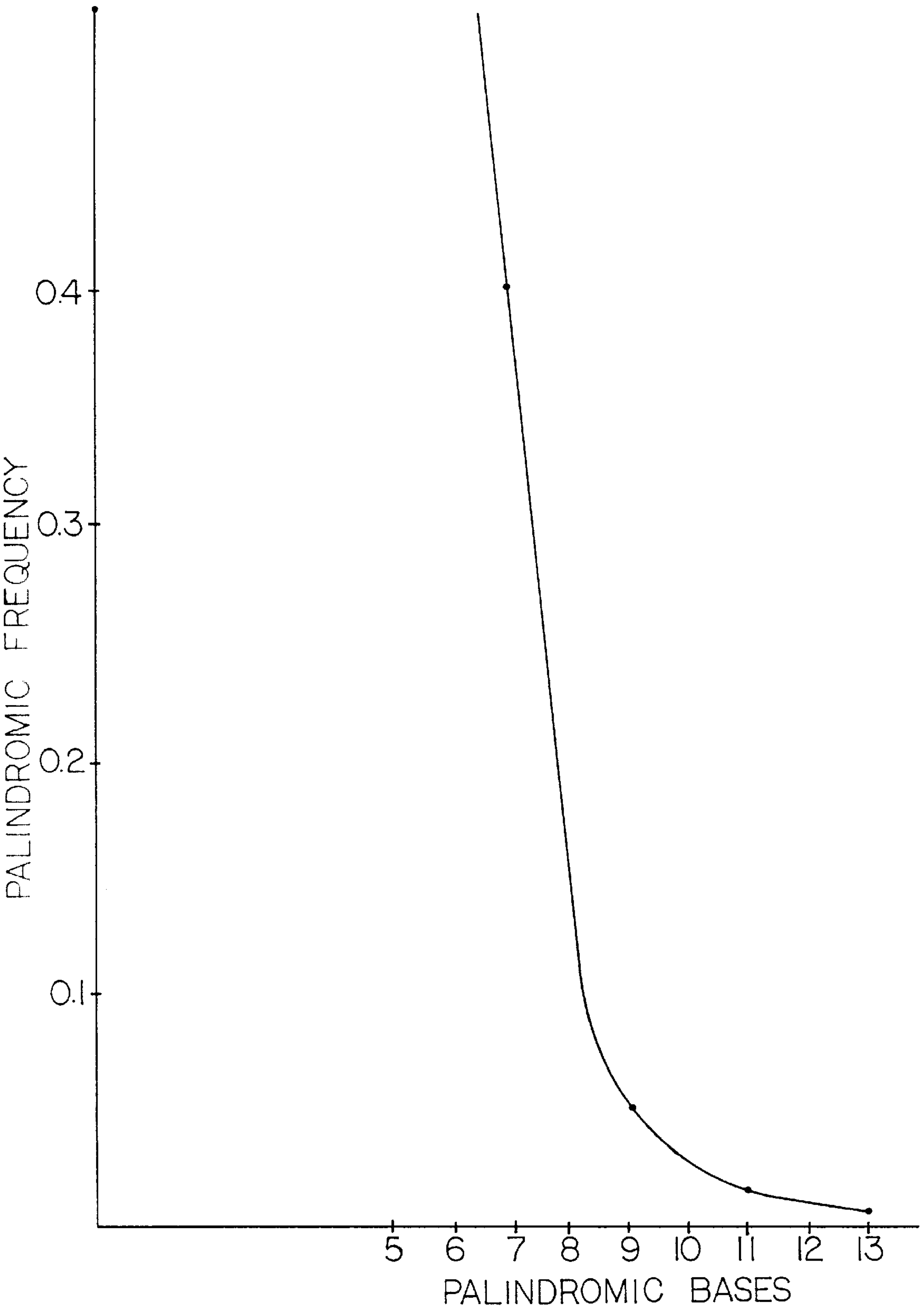
FIG. 11 shows the relationship between the palindromic frequency and the number of bases in a putative DNA primer, as determined by cDNA Matrix analysis.

In order to determine the frequency of occurrence or "palindromic frequency" of these anti-parallel repeats, a computer program called DNA Matrix (DNA Strider 1.2) was used to analyze double stranded cDNAs which were randomly selected from the GenBank database. DNA matrix analysis revealed the palindromic frequency of double strand cDNA to be surprisingly high and led to our development of a relationship between the number of bases in the chosen sequence, the "palindromic bases," and the palindromic frequency. Single strand cDNA (the mRNA strand) and its anti-parallel strand were compared, each from the 5' to 3' end by the DNA Matrix program. For example, as illustrated in FIG. 10, on the average, in every 202 bases of sequence in one strand of cDNA, there is one 9-base sequence that is exactly duplicated to that in another region of its antiparallel strand. The palindromic frequency found in native cDNA is much higher than that which would be calculated from random composition, suggesting that the nucleotide composition of double-stranded cDNA follows certain palindromic rules. As shown in FIG. 11, the palindromic frequency dramatically decreases when the number of bases in the searched segment increases. The key numbers of bases which lead to dramatic change of palindromic frequency are 9, 10 and 11 bases. This, then, is the theoretical basis for designing a primer for use in the DNA isolation and amplification method of the invention, palindromic PCR.

Table 1 presents the statistical data showing the palindromic frequency related to the number of bases in the searched segment.

TABLE 1

Palindromic Frequency Related to No. of Bases in Searched Segment as Revealed by cDNA Matrix Analysis

| No. Bases in Searched Segment (X Bases) | Average Length to Find One X-Base Palindromic Sequence | Palindromic Frequency |
|---|---|---|
| 7 bases | 18 bases | 0.4 |
| 9 bases | 202 bases | 0.048 |
| 11 bases | 872 bases | 0.015 |
| 13 bases | >1996 bases | <0.007 |

Figure 12:
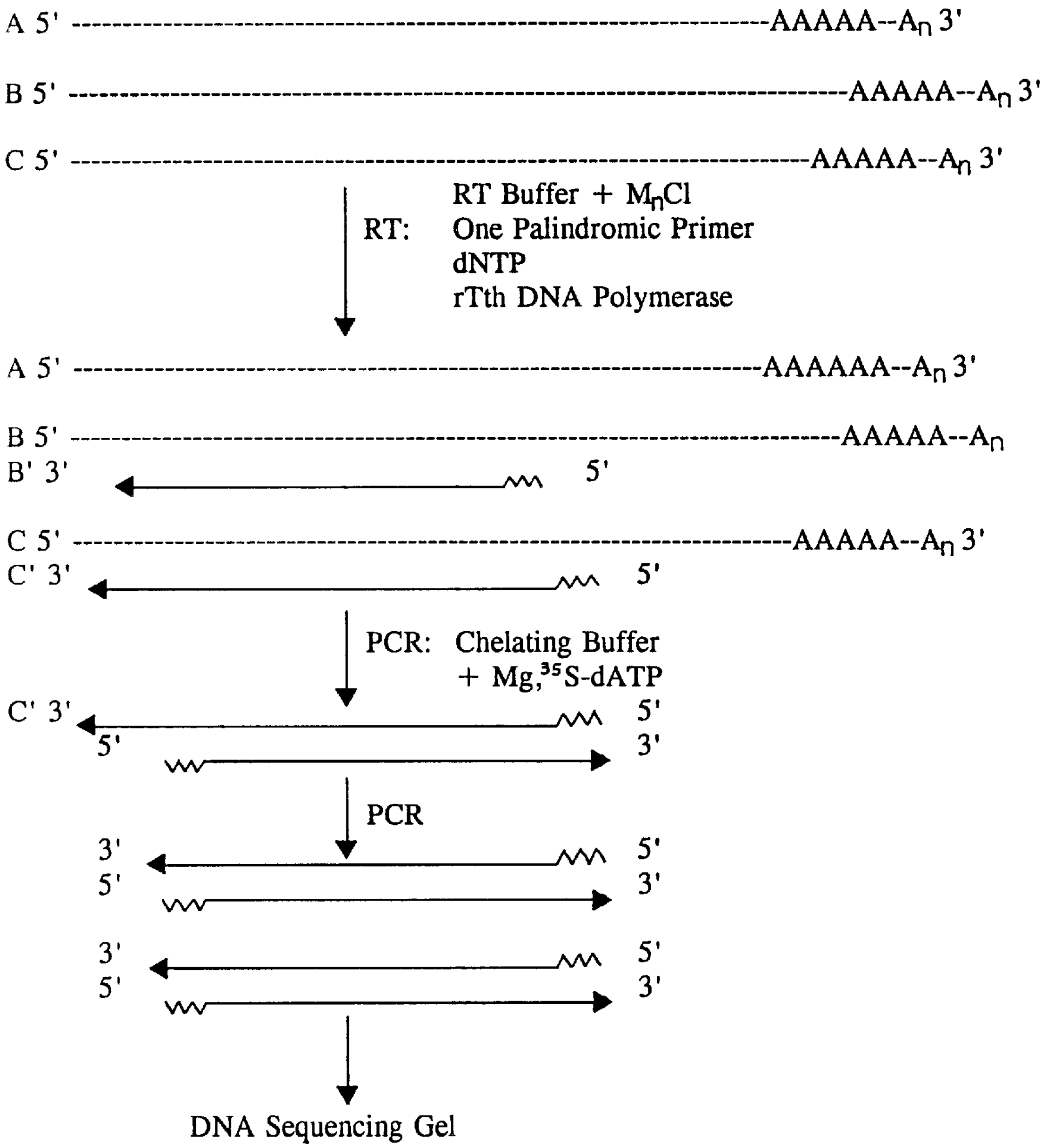
FIG. 12 is a schematic representation of the method of the invention, palindromic PCR, driven by the enzyme rTth DNA polymerase with one DNA primer in one reaction tube; the dotted line indicates mRNA and the solid line indicates cDNA; the short jagged line represents the single DNA primer.

The principle of the method of palindromic PCR is shown in schematic representation in FIG. 12. The general strategy is to use a single primer and one enzyme combining both reverse transcriptase and DNA polymerase activities, e.g., rTth DNA polymerase (from the thermophilic eubacterium Thermus thermophilus), to perform both reverse transcription and polymerase chain reaction in one reaction tube. rTth DNA polymerase possesses a very efficient reverse transcriptase activity in the presence of $MnCl_2$ and a thermostable DNA polymerase activity in the presence of $MgCl_2$. The rTth DNA polymerase has been observed to be greater than 100-fold more efficient in coupled reverse transcription and PCR than the analogous DNA polymerase, Taq (T. W. Myers et al., Biochemistry 30:7661, 1991). In this reaction, an appropriate primer would allow anchored annealing to some regions of certain mRNA species that contain sequence complementary to the palindromic primer. This subpopulation of mRNAs is likely to be reverse transcribed by rTth DNA polymerase. A "Palindromic" primer apparently has a greater probability of anchoring to the coding regions of mRNA than oligo dT primer. Once mRNAs are reverse transcribed to form a first strand cDNA species, the same primer can anneal to some regions of the first strand cDNA and function as the "Downstream primer" in a PCR reaction. The same primer can also function as the "Upstream primer." When the primer anchors to first strand cDNAs, the annealing position to various cDNA molecules should, in principle, be at different distances in different molecules from the first annealing position. Therefore, the amplified cDNA fragments from various mRNAs will be of different sizes. Once these PCR-generated cDNA fragments are labeled with $^{35}$S-dATP or $^{33}$P-dATP, they can be resolved as a ladder by DNA sequencing gels. A display of cDNAs originating from various mRNAs can then be visualized after autoradiography.

The selection of the specific palindromic primer depends on three important factors: the length, the GC content, and the sequence specificity. DNA Matrix analysis has indicated that the ideal length of a primer for an appropriate palindromic frequency is from 9 to 11 bases. Therefore, a set of primers from 8 base to 12 base in length with 50% GC content was chosen for study. Our results showed that 9, 10, and 11 base primers gave an appropriate number of cDNA fragments readily resolvable by DNA sequencing gels (FIG. 13). To identify the GC content of the primer most suitable for this method, a set of 10-mer primers with GC content ranging from 40% to 90% was tested. The results suggested that a GC content from 40% to 80% is acceptable (FIG. 13). However, primers with 40% to 60% GC content appear to yield better results. To examine the effect of the specific sequence of the primer, 10-mer primers of different sequences each having 50% GC content was tested. As predicted, different primers gave rise to different cDNA patterns (FIG. 13). As little a difference as three bases led to totally different cDNA profiles.

cDNA patterns generated by palindromic PCR are highly stable. When the same conditions were used but the experiments repeated at different times, the patterns of the amplified cDNA fragments were highly reproduced, indicating the reliability of this method.

In order to be sure of detecting mRNAs with a low copy number, it was necessary to determine the sensitivity of this method. It has been reported that the amplification driven by rTth DNA polymerase is at least 100-fold greater than that by Taq polymerase. rTth DNA polymerase allows the detection of IL-1a mRNA, which has a very low copy number, in 8 pg of total cellular RNA (T. W. Myers et al., *Biochemistry* 30:7661, 1991). Thus, the higher efficiency of rTth DNA polymerase ensures that the palindromic PCR method of the invention provides high sensitivity. In addition, because rTth polymerase is thermostable, it can also be used to perform several RT cycles (reverse transcription cycles), which means several copies of first strand cDNA can be obtained from a single copy of mRNA. The sensitivity of the method is increased by performing multiple RT cycles using rTth polymerase (FIG. 13).

The method of the invention was tested in a search for differences in mRNA expression between human colon carcinoma and the adjacent normal epithelium from a surgical specimen. Paired mRNA preparations were reverse transcribed with a palindromic primer 5'-CTGATCCATG (designated as PP-1 primer (SEQ ID NO: 16)) in the presence of $MnCl_2$ followed by PCR with the same primer in the presence of $MgCl_2$ using rTth DNA polymerase. The reaction products were then analyzed by DNA sequencing gels. About 70–110 amplified cDNA fragments ranging from 100–700 bases from both preparations were detected (FIG. 14). Whereas overall cDNA patterns between tumor and normal tissue are similar, significant differences were detected by this method. Most cDNA bands showed the same intensity between tumor and normal preparations, but two cDNA bands designated as TC1 and TC2 appeared with increased intensities in tumor tissue (FIG. 14). A sample reaction protocol is described below.

To 1.1 μl of double distilled (dd) $H_2O$ is added 0.5 μl of 10×rTth DNA polymerase reverse transcriptase (RT) buffer (100 mM Tris-Hcl, pH 8.3, 900 mM KCl) , 0.5 μl of 10 mM $MnCl_2$, 0.4 μl of 2.50 mM dNTP, 1.0 μl (0. 50 μg) of one palindromic primer (9–11 mer), and 1.0 μl (100 ng) of mRNA to form Mix A in a total vol. of 4.5 μl. Mix A is heated in a 0.5 ml PCR tube at 65° C. for 6 min and then at 37° C. for 8 min. Next, 0.5 μl (1.25 unit) of rTth DNA polymerase is added, the reaction mixture is mixed well, spun briefly, incubated at 70° C. for 12 min and then placed on ice. Mix B which consisting of 12.5 μl of dd $H_2O$, 2.0 μl of 10× chelating buffer (50% glycerol (v/v), 100 mM Tris-HCl, pH 8.3, 1M KCl, 0.5% Tween 20), 2.0 μl of 25 mM $MgCl_2$ solution, 2.50 nMdNTP and 2.0 μl of $^{35}$S-dATP (or $^{33}$P-dATP) is dispensed in the amount of 20 μl into each 5.0 μl RT reaction mixture. The samples are mixed and spun briefly and then overlaid with 25 μl of mineral oil. The polymerase chain reaction is then started: 94° C. for 40 sec., 40° C. for 2 min., 72° C. for 35 sec. (for 40 cycles, hold at 72° C. for 4 min.), and then 4° C.

For cDNA analysis, 7 μl of a PCR sample is mixed with 4 μl of sequencing loading buffer, samples are incubated at 80° C. for 3 min., and then placed on ice. 4.5 μl of the sample is loaded on a 6%–8% agarose DNA sequencing gel.

A gel slice containing a desirable cDNA band (such as TC1 ) was soaked in 200 μl of $ddH_2O$ for 20 min and then separated from 3M paper with a clean forcep or a plastic pipette tip. The gel was removed and pounded with an autoclaved plastic pipette tip. Elution buffer (20 μl) was added and the mixture was vortexed and left at room temperature for 4 hrs or overnight. After centrifugation, cDNA fragments in 10 μl eluent were reamplified by rTth DNA polymerase with the same palindromic primer, as described. After one 40-cycle PCR, the reamplified cDNA could be detected by agrose gels stained with ethidium bromide. The amount of cDNA generated was sufficient for cloning and preparing a probe for Northern Blot analysis. FIG. 15 shows the gel obtained when the TC1 cDNA band was subjected to elution and reamplification. Total PCR product of the TC1 fragment was 2.5 μg.

The reamplified TC1 cDNA fragment was treated with T4 DNA polymerase and cloned into pBluescript plasmid DNA vector at SmaI site by blunt end ligation. The nucleotide sequence of the TC1 fragment (SEQ ID NO: 1) showed that a sequence identical to the PP1 primer (SEQ ID NO: 16) is indeed present at the 5'-end of both strands of the TC1 fragment (FIG. 16). This result confirms that the 5'-ends of both complementary chains of the TC1 cDNA fragment used the same palindromic primer during palindromic PCR as discussed above. It also implies that the same palindromic primer sequence is present at the 5'-ends of both strands for every PCR product in the same reaction. These results establish that a single 9–11 base palindromic primer can effectively prime reverse transcription and then serve as both a “Downstream primer” and an “Upstream primer” in palindromic PCR amplification.

The method of the invention differs from other methods in a number of ways. In palindromic PCR, only a single primer (9–11 bases) is used and is sufficient to prime reverse transcription as well as to support subsequent PCR for a display of nearly 100 cDNA species. Because the pattern of amplified cDNAs depends on the sequence of the single palindromic primer, the species of mRNAs that are subjected to amplification can readily be controlled by a proper sequence of the palindromic primer. If a group or family of genes shares certain sequences, a primer can be chosen from such a sequence, and a specific display of this set of mRNAs can readily be performed. Likewise, computer analysis of the Genebank database may reveal additional sequences useful as a primer shared by a set of related genes. The use of such a primer by the method of the invention would allow the display for the expression of a given set of genes. Palindromic PCR provides an easy, sensitive and economical way to identify and isolate differentially expressed genes related to tumor and other disease.

Differential expression of TC1 DNA in normal tissue and tumor cells

Northern Blot analysis, as described above, confirmed the differential expression of TC1 mRNA in colon carcinoma tissue, and the absence of TC1 mRNA in the corresponding normal tissue. Evaluation of the expression of TC1 mRNA in additional cases of colon carcinoma at different stages was also undertaken. Surgical specimens of 24 cases of human primary colon carcinoma and 6 cases of liver metastases were examined by Northern hybridization of total RNA with $^{32}$P-labeled TC1 probe.

A Northern Blot of 24 pairs of colon carcinoma (T) and their adjacent normal tissue (N) probed with $^{32}$P-labeled TC1 cDNA is shown in FIG. 17. It is evident from the results that the level of TC1 mRNA in tumor tissue is much greater than the level in adjacent normal tissue in all 24 cases. The TC1 mRNA levels vary in different cases of carcinoma. Panels I and II show A: TC1 mRNA and B: Control; Panel III shows TC1 mRNA and control (Actin) mRNA.

FIG. 18 shows the Tumor/Normal RNA Ratio from Northern Blot results of FIG. 17. The horizontal line indicates the mean Tumor/Normal ratio. TC1 mRNA was abundantly expressed in all 24 cases of primary colon carcinoma and 6 cases of liver metastases, whereas only a small amount of TC1 mRNA was detected in a few cases of paired adjacent normal tissue. The mRNA level of TC1 was much greater in primary colon carcinoma than in paired adjacent normal colonic epithelium in all 24 cases. The Tumor/Normal ratio varied from 5.6 to 92, and the mean Tumor/Normal ratio being 32. The Tumor/Normal ratio, when plotted against the Duke's stage of disease, gave evidence for increasing TC1 expression with increasing stage of colon carcinoma.

In all six cases of paired colon carcinoma metastatic to liver, the TC1 mRNA level was much higher in metastatic tumor than in adjacent normal liver tissue. FIG. 19 shows a Northern Blot of RNA from metastatic colon carcinoma to liver (LM) and their adjacent normal liver (NL) probed with $^{32}$P-labeled TC1 cDNA. TC1 mRNA was expressed only in metastatic tumor in 5 of 6 samples. Only one sample of normal liver tissue expressed a very weak TC1 message. The Tumor/Normal ratio is greater than 64. These results suggested that differential expression of TC1 may be associated with human colorectal cancer progression and biological aggressiveness of the disease.

In vivo and in vitro expression of TC1 mRNA

The expression of TC1 mRNA in cultured cancer cells and in vivo tumor cells was analyzed and is described below. TC1 was overexpressed in tumor tissue in vivo. The expression of TC1 mRNA in cultured cancer cell lines in vitro was examined by Northern Blot analysis. RNAs isolated from twelve colon cancer cell lines (HT29, Clone A, MIP101, CX-1, Morser, CCL227, CCL228, etc.) derived from different stage of human colon carcinoma, two melanoma cell lines (LOX, A2058), one breast cancer cell line (MCF-7), two cervical cancer cell lines (Hela, A431), three bladder cancer cell lines (EJ, T24, MB49), one pancreas cancer cell line (CRL1420), two hepatoma cell lines (HepG2, HepG3) and four normal cell lines (FS-2, MRC-5, 498A, CV-1) were screened by Northern Blot analysis. However, the TC1 transcript could not be detected in all of these cell lines. This result suggested that TC1 expression was dramatically decreased or indeed turned off in cultured cancer cells. However, after cultured cancer cells were injected into nude mice to grow tumor in vivo, TC1 mRNA expression turned on again and its mRNA level could be detected by Northern Blot analysis.

FIG. 20 shows a Northern Blot of RNA from breast cancer cell line MCF-7 (1) and colon cancer cell line CX-1 (2) cultured in vitro, and MCF-7 tumor (3) and CX-1 tumor (4) grown in vivo in nude mice. TC1 mRNA in colon cancer cell line CX-1 and breast cancer cell line MCF-7 cultured in vitro could not be detected by Northern Blot analysis. After cultured CX-1 and HT29 cells were injected into nude mice to form tumors in vivo, TC1 mRNA was detectable by Northern Blot analysis, the TC1 mRNA levels being dramatically increased in vivo. This result suggests that TC1 gene expression was turned on or dramatically increased in the tumor cells in vivo. Thus, the differential expression of the TC1 gene appears to be related to invasion and metastasis of tumor cells in vivo. The regulation of TC1 gene expression in vivo and in vitro could be a very important model to understand tumorigenesis and tumor malignant behavior.

Expression of TC1 protein

Figure 21A:
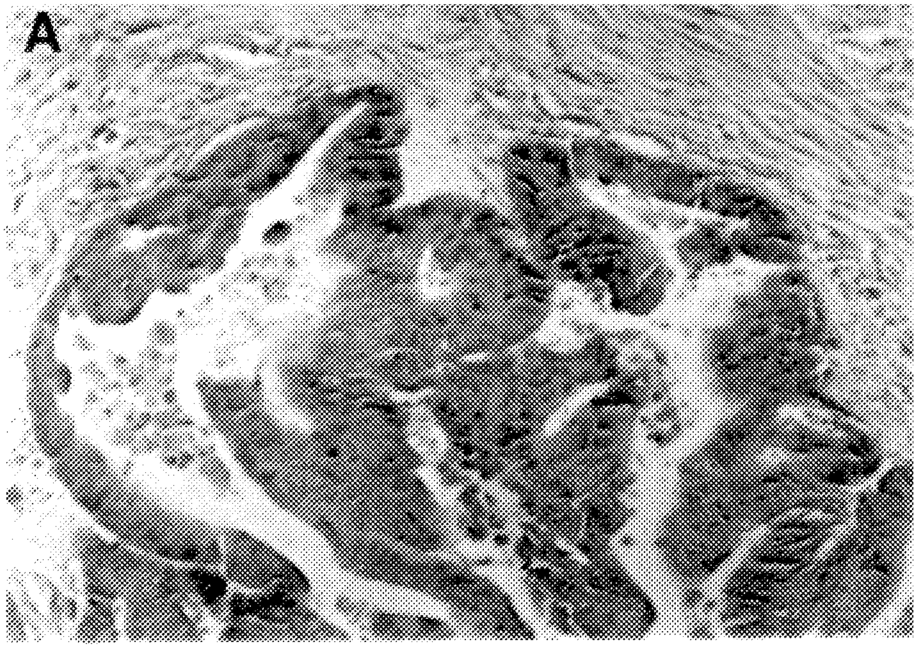
Figure 21B:
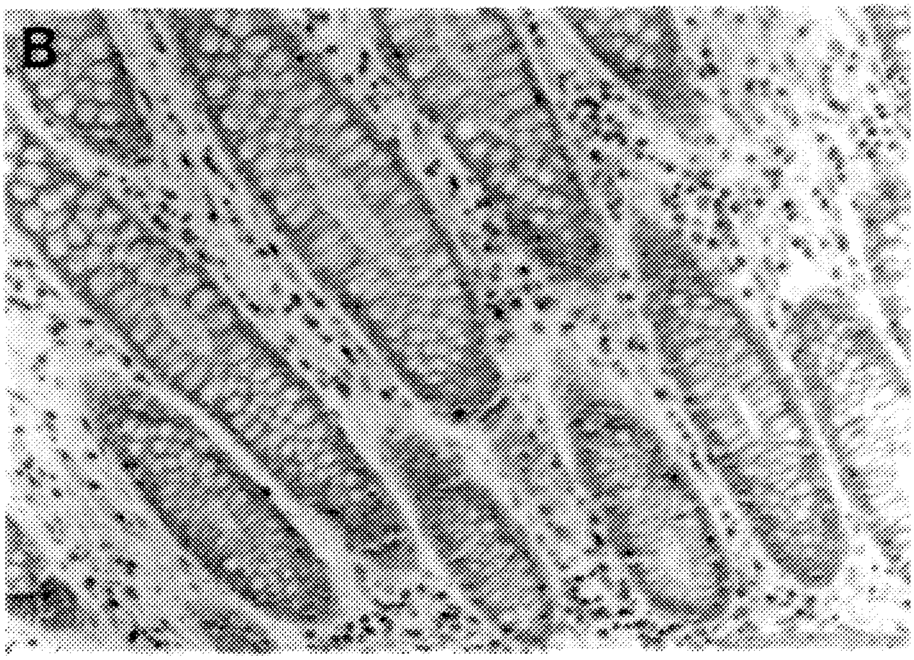
Figure 21C:
Figure 21D:
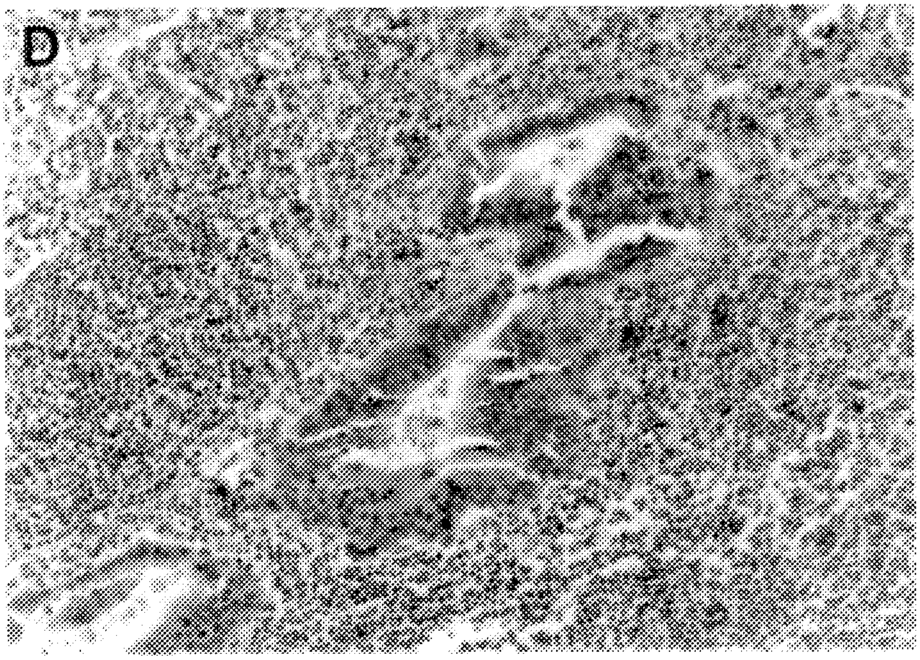
Figure 22A:
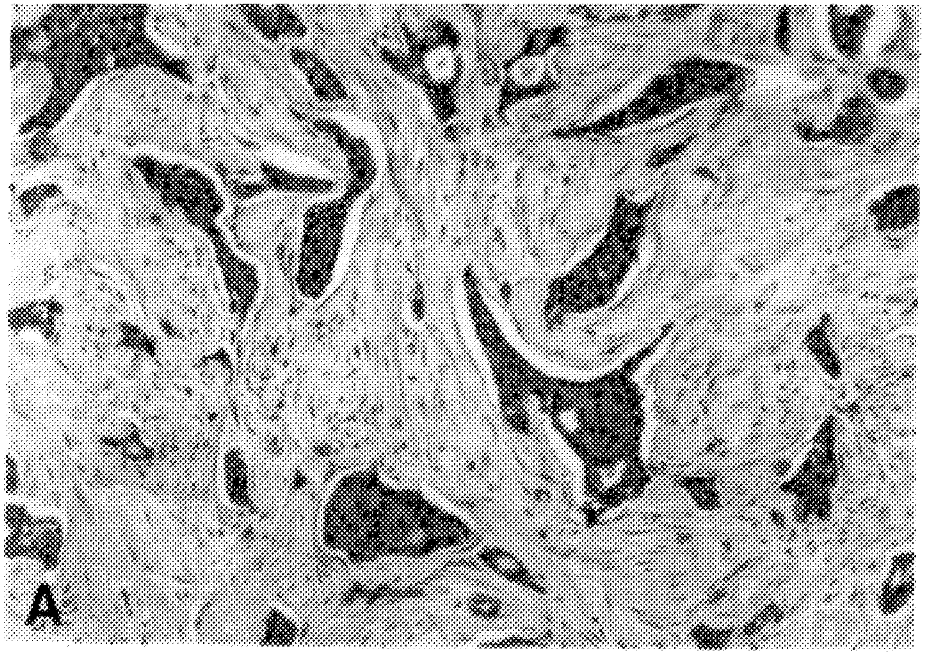
Figure 22B:
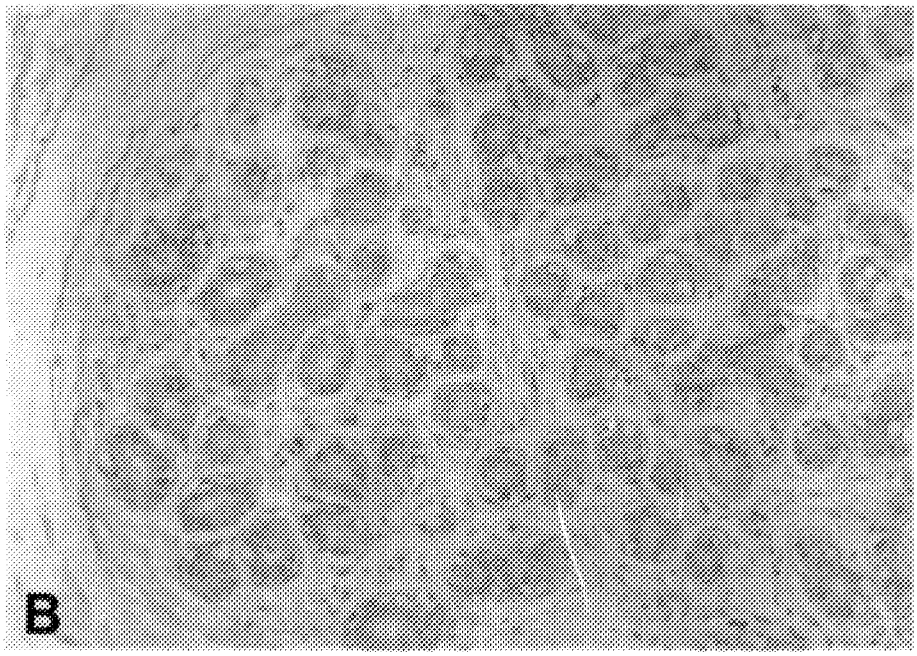
Figure 22C:
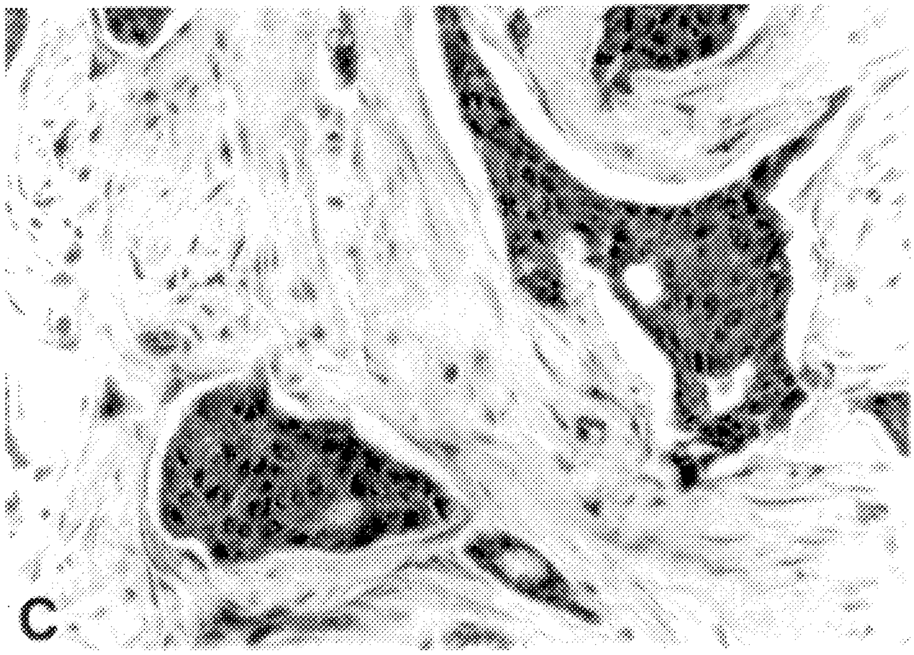
Figure 22D:
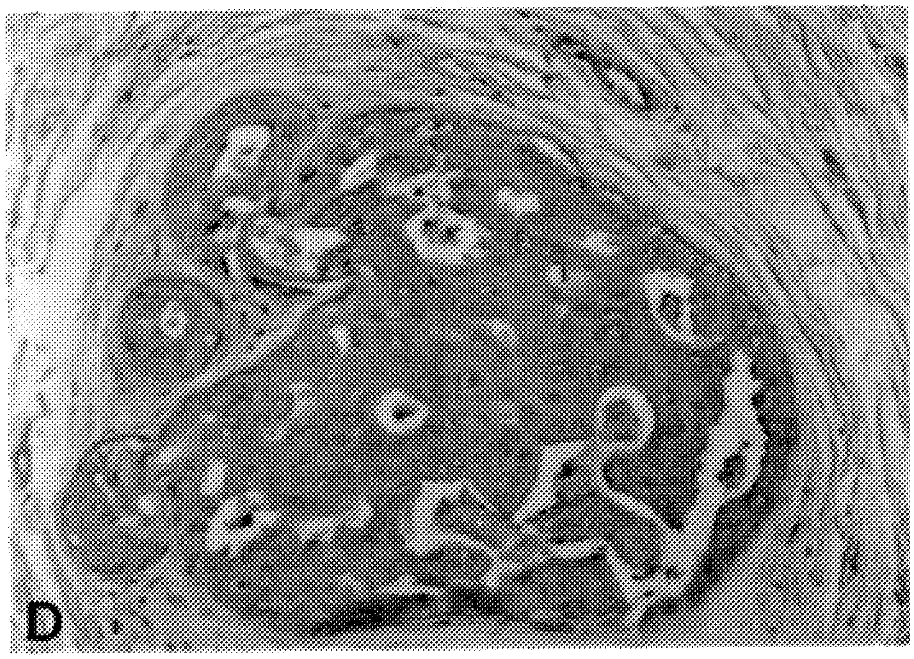
Figure 23A:
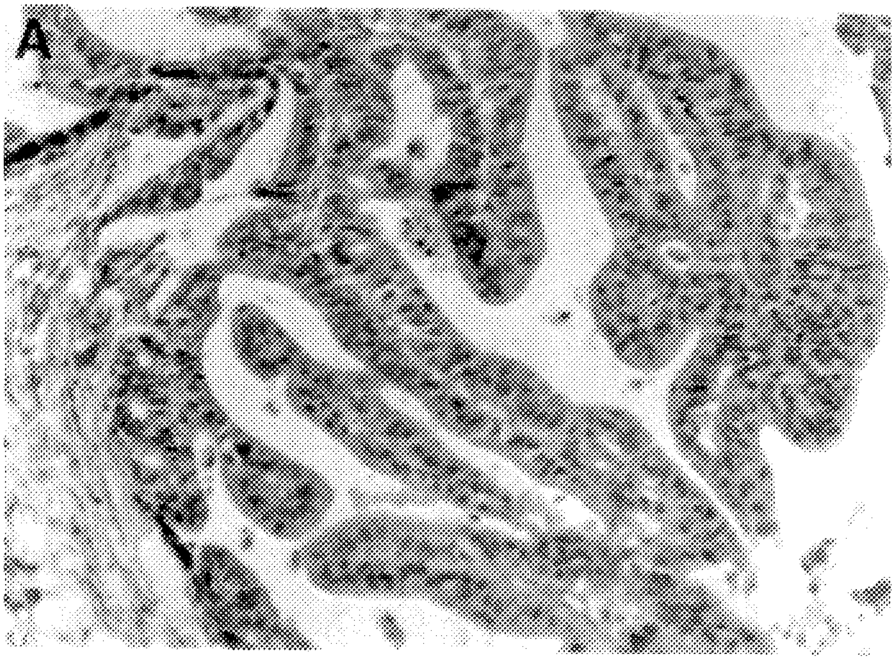
Figure 23B:
Figure 23C:
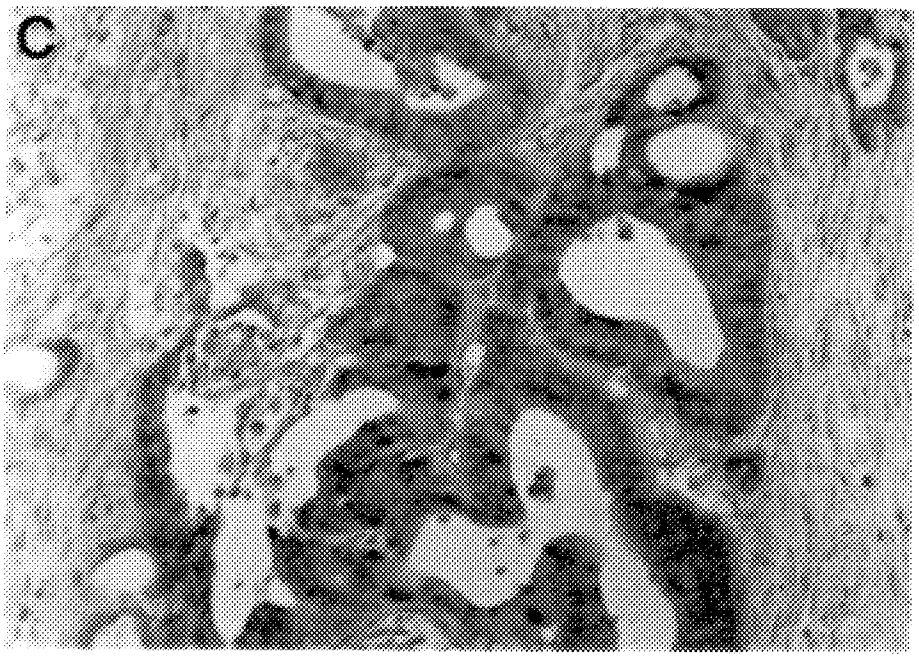
Figure 23D:
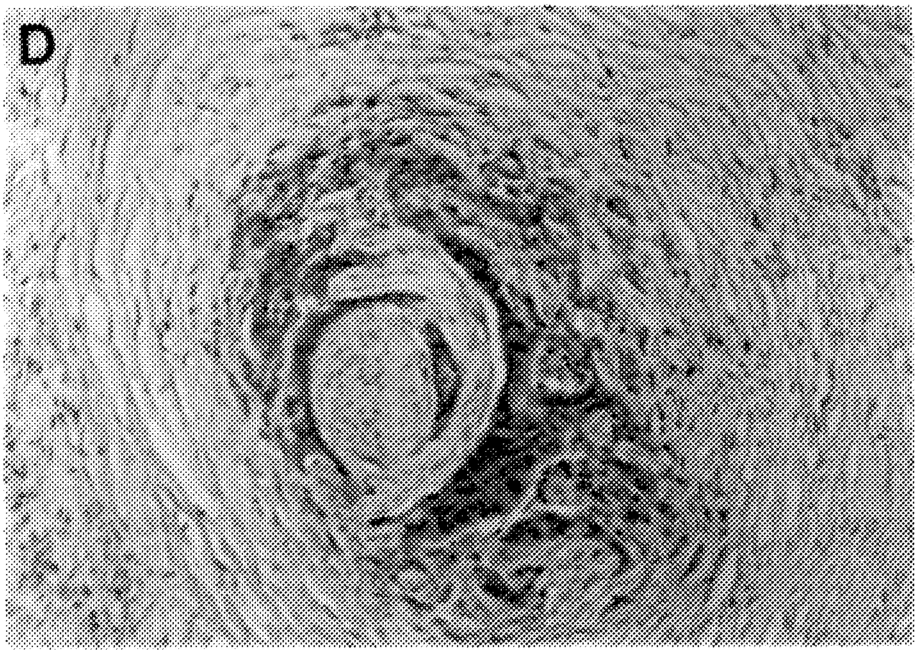

The expression of TC1 protein in in vivo tumor cells, cultured carcinoma cells, and in corresponding normal cells was examined, and is described below. The TC1 gene (SEQ ID NO:3) was cloned into a plasmid expression vector, and recombinant TC1 protein (SEQ ID NO:4) was expressed in bacteria. Several monoclonal antibodies against the bacterially-produced TC1 protein were raised, as will be described below. A variety of formalin-fixed and paraffin-embedded tumor tissue sections were examined by immunohistochemical staining with a mouse monoclonal anti-TC1 antibody anti-TC1-1 using an avidin-biotinylated-peroxidase detection technique. Strong positive staining of TC1 was found in primary colon carcinoma (FIG. 21, panel A), colon carcinoma metastatic to liver (FIG. 21, panel C) and lymph node (FIG. 21, panel D), breast carcinoma (FIG. 22, panels A, C, D) and gastric carcinoma (FIG. 23, panels A,B). The TC1 protein level in tumor tissue is much greater than the level of TC1 in adjacent normal tissue (FIGS. 21B, 23B).

These results, which represent the staining of sixteen cases of different stages of primary colon carcinoma, eight cases of colon tumor metastatic to liver and lymph node, fourteen cases of breast carcinoma and five cases of gastric carcinoma, suggested the following three conclusions. First, the TC1 protein level appeared to be different in different types of carcinoma, with protein levels being highest in breast carcinoma. Second, the advance edge of the deeper invasive tumor appeared stain stronger for TC1, suggesting a greater prevalence of TC1 protein at the advance edge of the tissue. Third, the move advanced stages of tumor appeared to contain more TC1 protein.

FIG. 24 is a Western Blot analysis of protein samples from two pairs of colon carcinoma and their adjacent normal colon (A) and two pairs of breast carcinoma and their adjacent normal breast (B), using a monoclonal antibody against TC1 protein as a probe. A major 86 kd protein (arrow) was detected by anti-TC1 antibody in tumor samples (T) but not in normal samples (N). The Western Blot analysis confirmed that tumor tissue contained significantly more TC1 protein than the corresponding adjacent normal tissue.

TC1 gene expression

The presence of TC1 mRNA and protein in malignant mesothelioma cells was examined, and is described below. More than 42 cell lines have been screened for TC1 gene expression by Northern Blot analysis. However, only two cell lines, JMN1B and JMN, express detectable mRNA by Northern Blot analysis. JMN1B and JMN are malignant mesothelioma, JMN1B being a subline of JMN cells with showing enhanced tumorigenicity after passage of JMN cells through a nude mouse. FIG. 25 is a Northern Blot analysis of RNA from malignant mesothelioma cells JMNlB and JMN using TC1 cDNA as a probe. The results presented in Panel 25B demonstrate that TC1 mRNA level in JMN1B cells (2) is much greater than that in JMN cells (1). Panel 25A shows the ethidum bromide staining pattern of an RNA gel in which the same amount of JMN (1) and JMN1B (2) RNA is loaded per lane.

The Northern Blot analysis revealed that the TC1 mRNA level is much higher in JMN1B than in JMN, the JMN1B/JMN ratio being approximately 14. Higher expression of TC1 mRNA in JMN1B could be related to the observed greater tumorigenicity of JMN1B cells. It has been found that JMN1B cells can secrete an "EGF-like" growth factor called transformed mesothelial growth factor (TMGF) that satisfies the EGF requirement of normal human mesothelial cells. The difference in the levels of TC1 mRNA in JMN1B and JMN cells provides an ideal cell model to understand the regulation of TC1 expression and its relation to tumorigenicity.

Sequence analysis of the deduced amino acid sequence has revealed that the TC1 protein (SEQ ID NO: 4) contained a secretory leader signal at its N-terminus. The secretion of TC1 protein was confirmed by Wester Blot analysis of conditioned medium of JMN1B cells. JMN1B cells were cultured in regular medium until 90% confluent, then cultured in serum free medium for two days. This serum free conditioned medium was analyzed by immunoblotting with anti-TC1 monoclonal antibody. FIG. 26 is a Western blot analysis using a monoclonal antibody against TC1 to probe JMN1B cells grown in conditioned medium and whole cell lysate. Two major bands (about 86 kd and 104 kd) were recognized by anti-TC1 antibody both in JMN1B cell conditioned medium (1) and whole cell lysate (2). Numbers on the left indicate the position of molecular weight standards in kilodalton. The protein size of the lower molecular weight 86 kd band is consistent with that of deduced TC1 protein, whereas the higher molecular weight 104 kd band is consistent with a TC1 glycoprotein. There is one predicted site of N-linked glycosylation at the amino acid residue 605 (NDT) of deduced TC1 protein sequence. There are 60 threonine residues and 36 serine residues in the deduced TC1 sequence, each of which is a potential site of O-linked glycosylation.

Human malignant mesothelioma cell line JMN1B can express abundant TC1. This cell line was used to study the distribution and localization of TC1 protein by immunofluorescent staining with an anti-TC1 monoclonal antibody followed by Rhodamine conjugated goat anti-mouse IgG secondary antibody. When JMN1B cells were fixed with paraformaldehyde without subsequent permeabilization, the positive staining was seen on the cell surface or outside of the cell (FIG. 27, panels A, B), which confirms the secretion of TC1 protein. When JMN1B cells were fixed with paraformaldehyde and then permeabilized, positive staining appeared in the Golgi complex and the endoplasmic reticulum (ER) in the cell (FIG. 27, panels C,D), suggesting that TC1 protein is synthesized in the ER and Golgi complex. The staining in the Golgi complex is clearly evident, indicating that glycosylation of TC1 protein may be located in the Golgi complex. The TC1 protein distribution pattern also suggests that TC1 is a secreted glycoprotein.

Without being bound to one theory as to the biological function of TC1, observations as to the prevalence and expression of TC1 mRNA and protein indicate that TC1 may be related to tumor malignant behavior such as invasion and metastases. These observations include the following: TC1 is significantly overexpressed in tumor tissue; TC1 is a secreted protein; later stage tumor expresses higher levels of TC1; deeper invasive tumor contains higher levels of TC1 protein; TC1 expression turns off in cultured tumor cells in vitro and turns on again after cells grow tumor tissue in vivo. These observations indicate that the function of TC1 is not related to tumor cell proliferation, but is more likely involved in tumor malignant behavior in vivo, such as invasion and metastases.

TC1 is a member of a Family of Proteins

Figure 8:
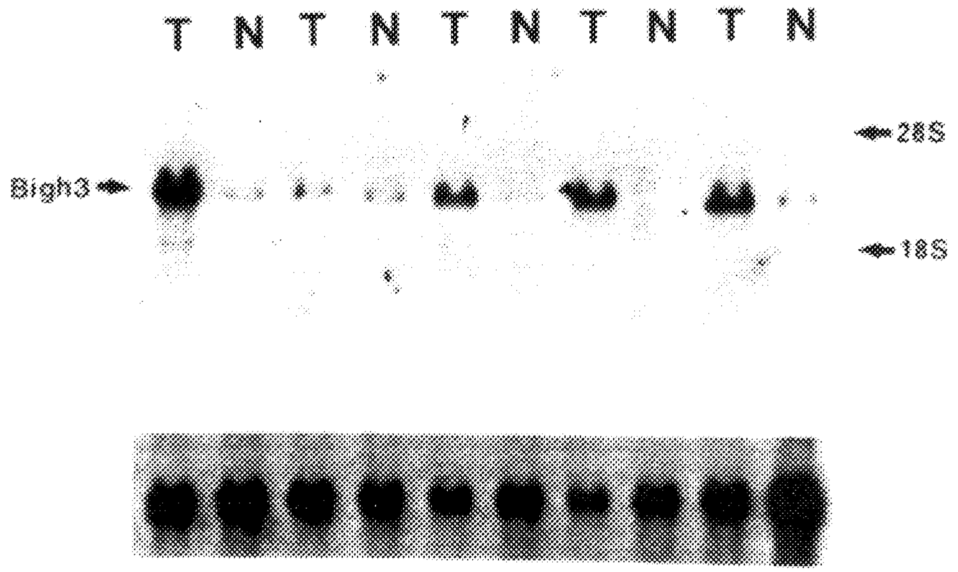
FIG. 8 is a Northern Blot of five pairs of RNA from colon carcinoma (T) and adjacent normal colon tissue (N) probed with 32P-labeled Big-h3 cDNA, the bottom panel representing control RNA probed with 32P-labeled B-actin.

A FASTA search of the GenBank and EMBL database with the TC1 open reading frame indicated that the protein is unique. However, TC1 whole protein shared 45% sequence identity with a TGF-beta inducible gene, Big-h3, at the amino acid level, suggesting that TC1 and Big-h3 may belong to a new gene family. The identity between TC1 (SEQ ID NO: 4) and Big-h3 (SEQ ID NO: 17) at the amino acid level is shown in FIG. 7. In FIG. 7, identical amino acids between TC1 and Big-h3 are boxed. Several stretches of amino acids GSFTXFAPSNEAW (see SEQ ID NO: 4, amino acid residues 136–148 ), TLXAPTNEAFEKXP (see SEQ ID NO: 4, amino acid residues 276–287), ATNGVVHXIDXV (see SEQ ID NO: 4, amino acid residues 224–235), LYXGQXLETXGGKXLRVFVYR (see SEQ ID NO: 4, amino acid residues 449–469), HYPNGXVTVNCAR (see SEQ ID NO: 4, amino acid residues 204–216) are highly conserved between TC1 and Big-h3 (compare SEQ ID NO: 4 with SEQ ID NO:17). Northern Blot analysis showed that the TC1 gene is expressed from a larger transcript than Big-h3, and DNA sequence analysis indicated that TC1 contains a longer open reading frame encoding a higher molecular weight protein than the Big-h3 gene. It has been found that Big-h3 also contains four internal repeats. The amino acid sequence homology and structural similarity between TC1 and Big-h3 indicate their functional similarity and relationship. We found that Big-h3 mRNA is also much more abundant in colon carcinoma tissue than in adjacent normal colon tissue (FIG. 7). FIG. 8 is a Northern Blot of five pairs of RNA from colon carcinoma (T) and adjacent normal colon tissue (N) probed with $^{32}$P-labeled Big-h3 cDNA. The blot shows Big-h3 mRNA level in colon carcinoma to be much higher than that in adjacent normal tissue. The bottom panel represents control RNA probed with $^{32}$P-labeled B-actin.

In contrast to the expression pattern of TC1 mRNA, which is shown to be largely restricted to in vivo tumor tissue, Big-h3 mRNA is not only expressed in the tumor tissue, but also expressed in the cultured tumor cell lines and some normal cell lines. Though TC1 and Big-h3 shared significant homology, their responses to growth factors are distinctly different.

Fasciclin I, II, III are extrinsic membrane glycoproteins involved in the growth cone guidance during nervous system development in the insect embryo. A search of NBRF protein database revealed a significant homologous domain between TC1 and Fasciclin I from Grasshopper and Drosophila. One TC1 domain of 204 amino acids (amino acid residue 503–706) shared 30% identity with Grasshopper Fasciclin I, and shared 25% identity with Drosophila Fasciclin. FIG. 9 shows amino acid sequence homology between TC1 (SEQ ID NO: 4) and Fasciclin I from Grasshopper (GrF) (SEQ ID NO: 18) and Drosophila (DrF) (SEQ ID NO: 19). Boxed amino acids are identical with at least one other amino acid at that same position.

It has been found that Fasciclin also contained four internal homologous domains, each consisting of approximately 150 amino acids. The domains of TC1 and Fasciclin I share some highly conserved amino acid stretches such as TXFV/APTNXAF (see SEQ ID NO: 4), amino acid residues 538–547), and VXHVVDXXLXP compare SEQ ID NO: 4 SEQ ID NOS: 18 and 19) (see SEQ ID NO: 4, amino acid residues 626–636).

The most conserved sequence among TC1, Big-h3 and Fasciclin is TXFA/VPTNXAF/W (see SEQ ID NO: 4, amino acid residues 538–547). All four internal repeats in TC1 or Big-h3 or Fasciclin I also share the most conserved sequence TXFA/VPT/SNXAF/W (see SEQ ID NO: 4, amino acid residues 538–547). This sequence appears to be an important motif of this gene family.

Screening for antagonists to TC1 function

The invention also includes methods of screening for agents which inhibit TC1 gene expression, whether such inhibition be at the transcriptional or translational level.

Screening methods, according to the invention, for agents which inhibit expression of the TC1 gene in vitro will include exposing a metastatic cell line in which TC1 mRNA is detectable in culture to an agent suspected of inhibiting production of the TC1 mRNA; and determining the level of TC1 mRNA in the exposed cell line, wherein a decrease in the level of TC1 mRNA after exposure of the cell line to the agent is indicative of inhibition of TC1 mRNA production.

Alternatively, such screening methods may include in vitro screening of a metastatic cell line in which TC1 protein is detectable in culture to an agent suspected of inhibiting production of the TC1 protein; and determining the level of TC1 protein in the cell line, wherein a decrease in the level of TC1 protein after exposure of the cell line to the agent is indicative of inhibition of TC1 protein production.

The invention also encompasses in vivo methods of screening for agents which inhibit expression of the TC1 gene, comprising exposing a mammal having tumor cells in which TC1 mRNA or protein is detectable to an agent suspected of inhibiting production of TC1 mRNA or protein; and determining the level of TC1 mRNA or protein in tumor cells of the exposed mammal. A decrease in the level of TC1 mRNA or protein after exposure of the mammal to the agent is indicative of inhibition of TC1 gene expression.

According to the invention, agents can be screened in vitro or in vivo as follows. For in vitro screening, a metastatic cell line, e.g., JMN1B, may be cultured in vitro and exposed to an agent suspected of inhibiting TC1 expression in an amount and for a sufficient to inhibit such expression. For in vivo screening, a mammal afflicted with a late stage cancer, particularly one of breast cancer, colon cancer, or cancer of the gastrointestinal tract, is exposed to the agent at a dosage and for a time sufficient to inhibit expression of TC1. A late stage cancer is defined by the Duke's stage of the cancer; i.e., late stage cancers correspond to Duke's stages 3–4. The amount or dosage of the agent which is effective to inhibit TC1 expression may be determined using serial dilutions of the agent. The level of TC1 mRNA or protein may be determined using an aliquot of cells from the cell culture or the in vivo tumor and performing Northern Blot analysis or Western Blot analysis, respectively. The agent will be considered inhibitory if the level of TC1 mRNA or protein decreases by more than 50%, and preferably more than 70–80%, relative to the same cell line which has not been exposed to the agent. Examples of potential inhibitors of TC1 mRNA or protein production include but are not limited to antisense RNA, competitive inhibitors of the TC1 protein such as fragments of the TC1 protein itself, or antibodies to TC1 protein. Candidate TC1 inhibitory fragments include, but are not limited to, TL/YFA/VPT/SNE/DAF/W (see SEQ ID NO: 4, amino residues 276–285) and NGV/AI/VHXI/VD/F (see SEQ ID NO: 4, amino acid residues 361–368).

Use of antagonists to TC1 functions

The invention also encompasses the treatment of late stage cancers by administration to a mammal afflicted with a late stage cancer one or more of the above-selected inhibitory agents. Late stage cancers, particularly those of the breast, colon, or gastrointestinal tract, are treated according to the invention by administering the inhibitory agent to a mammal afflicted with a late stage cancer in an amount and for a time sufficient to decrease the level of TC1 protein or mRNA.

The mode of administration may be intra-venously, intraperitoneally, by intra-muscular or intra-dermal injection, or orally. Administration may be by single dose, or may be continuous or intermittent. The dosage of inhibitory agent is that dosage which is effective to inhibit TC1 production, i.e., within the range of 10 μg/kg body weight-100 gm/kg body weight, preferably, within the range of 1 mg/kg body weight-1 gm/kg body weight, most preferably 10–100 mg/kg body weight.

Production of monoclonal antibodies reactive with TC1

An anti-TC1 antibody is produced according to Kohler and Milstein, *Nature,* 256:495–497 (1975), Eur. *J. Immunol.* 6:511–519 (1976), both of which are hereby incorporated by reference, using the TC1 protein or a fragment thereof as the immunizing antigen. Hybridomas produced by the above process are selected for anti-TC1 antibodies using the TC1 as an antigen in an ELISA assay. The single type of immunoglobulin produced by a such a hybridoma is specific for a single antigenic determinant, or epitope, on the TC1 antigen. Certain TC1-specific antibodies, for example, anti-TC1-1 produced by the hybridoma deposited with the American Type Culture Collection (ATCC) under the ATCC number HB 11481, are unique in that they recognize the TC1 protein, more specifically an epitope of the TC1 protein, in formaldehyde-fixed and paraffin-embedded tumor cells which bear TC1. Often TC1 antigenic portion is destroyed by this tissue treatment process such that the antibody will no longer recognize its cognate epitope.

Deposits

The following samples were deposited on Oct. 29, 1993, with the American Type Culture Collection (ATCC), 12301 Parklawn Drive, Rockville, Md. 20852.

| Deposit | ATCC Accession No. |
|---|---|
| TC1 gene in pBluescript plasmid DNA vector | HB 11481 |
| Hybridoma TC-1 | 75599 |

Applicants assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1,14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

OTHER EMBODIMENTS

The invention is not limited to those embodiments described herein, but may encompass modifications and variations which do not depart from the spirit of the invention. While the invention has been described in connection with specific embodiments thereof, it will be understood that further modifications are within the scope of the following claims.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 636 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 1..636

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CTG | ATC | CAT | GGG | AAC | CAG | ATT | GCA | ACA | AAT | GGT | GTT | GTC | CAT | GTC | ATT | 48 |
| Leu | Ile | His | Gly | Asn | Gln | Ile | Ala | Thr | Asn | Gly | Val | Val | His | Val | Ile | |
| 1 | | | | 5 | | | | | 10 | | | | | 15 | | |
| GAC | CGT | GTG | CTT | ACA | CAA | ATT | GGT | ACC | TCA | ATT | CAA | GAC | TTC | ATT | GAA | 96 |
| Asp | Arg | Val | Leu | Thr | Gln | Ile | Gly | Thr | Ser | Ile | Gln | Asp | Phe | Ile | Glu | |
| | | | 20 | | | | | 25 | | | | | 30 | | | |
| GCA | GAA | GAT | GAC | CTT | TCA | TCT | TTT | AGA | GCA | GCT | GCC | ATC | ACA | TCG | GAC | 144 |
| Ala | Glu | Asp | Asp | Leu | Ser | Ser | Phe | Arg | Ala | Ala | Ala | Ile | Thr | Ser | Asp | |
| | | 35 | | | | | 40 | | | | | 45 | | | | |
| ATA | TTG | GAG | GCC | CTT | GGA | AGA | GAC | GGT | CAC | TTC | ACA | CTC | TTT | GCT | CCC | 192 |
| Ile | Leu | Glu | Ala | Leu | Gly | Arg | Asp | Gly | His | Phe | Thr | Leu | Phe | Ala | Pro | |
| | 50 | | | | | 55 | | | | | 60 | | | | | |
| ACC | AAT | GAG | GCT | TTT | GAG | AAA | CTT | CCA | CGA | GGT | GTC | CTA | GAA | AGG | ATC | 240 |
| Thr | Asn | Glu | Ala | Phe | Glu | Lys | Leu | Pro | Arg | Gly | Val | Leu | Glu | Arg | Ile | |
| 65 | | | | | 70 | | | | | 75 | | | | | 80 | |
| ATG | GGA | GAC | AAA | GTG | GCT | TCC | GAA | GCT | CTT | ATG | AAG | TAC | CAC | ATC | TTA | 288 |
| Met | Gly | Asp | Lys | Val | Ala | Ser | Glu | Ala | Leu | Met | Lys | Tyr | His | Ile | Leu | |
| | | | | 85 | | | | | 90 | | | | | 95 | | |
| AAT | ACT | CTC | CAG | TGT | TCT | GAG | TCT | ATT | ATG | GGA | GGA | GCA | GTC | TTT | GAG | 336 |
| Asn | Thr | Leu | Gln | Cys | Ser | Glu | Ser | Ile | Met | Gly | Gly | Ala | Val | Phe | Glu | |
| | | | 100 | | | | | 105 | | | | | 110 | | | |
| ACG | CTG | GAA | GGA | AAT | ACA | ATT | GAG | ATA | GGA | TGT | GAC | GGT | GAC | AGT | ATA | 384 |
| Thr | Leu | Glu | Gly | Asn | Thr | Ile | Glu | Ile | Gly | Cys | Asp | Gly | Asp | Ser | Ile | |
| | | 115 | | | | | 120 | | | | | 125 | | | | |
| ACA | GTA | AAT | GGA | ATC | AAA | ATG | GTG | AAC | AAA | AAG | GAT | ATT | GTG | ACA | AAT | 432 |

-continued

Thr Val Asn Gly Ile Lys Met Val Asn Lys Lys Asp Ile Val Thr Asn
130 135 140

AAT GGT GTG ATC CAT TTG ATT GAT CAG GTC CTA ATT CCT GAT TCT GCC 480
Asn Gly Val Ile His Leu Ile Asp Gln Val Leu Ile Pro Asp Ser Ala
145 150 155 160

AAA CAA GTT ATT GAG CTG GCT GGA AAA CAG CAA ACC ACC TTC ACG GAT 528
Lys Gln Val Ile Glu Leu Ala Gly Lys Gln Gln Thr Thr Phe Thr Asp
165 170 175

CTT GTG GCC CAA TTA GGC TTG GCA TCT GCT CTG AGG CCA GAT GGA GAA 576
Leu Val Ala Gln Leu Gly Leu Ala Ser Ala Leu Arg Pro Asp Gly Glu
180 185 190

TAC ACT TTG CTG GCA CCT GTG AAT AAT GCA TTT TCT GAT GAT ACT CTC 624
Tyr Thr Leu Leu Ala Pro Val Asn Asn Ala Phe Ser Asp Asp Thr Leu
195 200 205

AGC ATG GAT CAG 636
Ser Met Asp Gln
210

( 2 ) INFORMATION FOR SEQ ID NO:2:

( i ) SEQUENCE CHARACTERISTICS:
( A ) LENGTH: 212 amino acids
( B ) TYPE: amino acid
( D ) TOPOLOGY: linear ( i i ) MOLECULE TYPE: protein ( x i ) SEQUENCE DESCRIPTION: SEQ ID NO:2:

Leu Ile His Gly Asn Gln Ile Ala Thr Asn Gly Val Val His Val Ile
1 5 10 15

Asp Arg Val Leu Thr Gln Ile Gly Thr Ser Ile Gln Asp Phe Ile Glu
20 25 30

Ala Glu Asp Asp Leu Ser Ser Phe Arg Ala Ala Ala Ile Thr Ser Asp
35 40 45

Ile Leu Glu Ala Leu Gly Arg Asp Gly His Phe Thr Leu Phe Ala Pro
50 55 60

Thr Asn Glu Ala Phe Glu Lys Leu Pro Arg Gly Val Leu Glu Arg Ile
65 70 75 80

Met Gly Asp Lys Val Ala Ser Glu Ala Leu Met Lys Tyr His Ile Leu
85 90 95

Asn Thr Leu Gln Cys Ser Glu Ser Ile Met Gly Gly Ala Val Phe Glu
100 105 110

Thr Leu Glu Gly Asn Thr Ile Glu Ile Gly Cys Asp Gly Asp Ser Ile
115 120 125

Thr Val Asn Gly Ile Lys Met Val Asn Lys Lys Asp Ile Val Thr Asn
130 135 140

Asn Gly Val Ile His Leu Ile Asp Gln Val Leu Ile Pro Asp Ser Ala
145 150 155 160

Lys Gln Val Ile Glu Leu Ala Gly Lys Gln Gln Thr Thr Phe Thr Asp
165 170 175

Leu Val Ala Gln Leu Gly Leu Ala Ser Ala Leu Arg Pro Asp Gly Glu
180 185 190

Tyr Thr Leu Leu Ala Pro Val Asn Asn Ala Phe Ser Asp Asp Thr Leu
195 200 205

Ser Met Asp Gln
210

( 2 ) INFORMATION FOR SEQ ID NO:3:

-continued ( i ) SEQUENCE CHARACTERISTICS:
( A ) LENGTH: 3126 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 43..2376

( x i ) SEQUENCE DESCRIPTION: SEQ ID NO:3:

```
GCCACCATGT AGCCCGCGTC ACCGTTCTGC GCATTCCGCA GC ATG GCT CTG CCT       54
                                              Met Ala Leu Pro
                                               1

GCC CGA ATC CTC GCT CTG GCC CTC GCA CTG GCG CTC GGA CCC GCC GTG     102
Ala Arg Ile Leu Ala Leu Ala Leu Ala Leu Ala Leu Gly Pro Ala Val
  5                  10                  15                  20

ACA CTG GCC AAC CCG GCG AGA ACG CCG TAC GAG CTG GTA CTC CAG AAG     150
Thr Leu Ala Asn Pro Ala Arg Thr Pro Tyr Glu Leu Val Leu Gln Lys
                 25                  30                  35

AGC TCG GCA CGA GGG GGT CGG GAC CAA GGC CCA AAT GTC TGT GCC CTT     198
Ser Ser Ala Arg Gly Gly Arg Asp Gln Gly Pro Asn Val Cys Ala Leu
             40                  45                  50

CAA CAG ATT TTG GGC ACC AAA AAG AAA TAC TTC AGC ACT TGT AAG AAC     246
Gln Gln Ile Leu Gly Thr Lys Lys Lys Tyr Phe Ser Thr Cys Lys Asn
         55                  60                  65

TGG TAT AAA AAG TCC ATC TGT GGA CAG AAA ACG ACT GTG TTA TAT GAA     294
Trp Tyr Lys Lys Ser Ile Cys Gly Gln Lys Thr Thr Val Leu Tyr Glu
     70                  75                  80

TGT TGC CCT GGT TAT ATG AGA ATG GAA GGA ATG AAA GGC TGC CCA GCA     342
Cys Cys Pro Gly Tyr Met Arg Met Glu Gly Met Lys Gly Cys Pro Ala
 85                  90                  95                 100

GTT TTG CCC ATT GAC CAT GTT TAT GGC ACT CTG GGC ATC GTG GGA GCC     390
Val Leu Pro Ile Asp His Val Tyr Gly Thr Leu Gly Ile Val Gly Ala
                105                 110                 115

ACC ACA ACG CAG CGC TAT TCT GAC GCC TCA AAA CTG AGG GAG GAG ATC     438
Thr Thr Thr Gln Arg Tyr Ser Asp Ala Ser Lys Leu Arg Glu Glu Ile
            120                 125                 130

GAG GGA AAG GGA TCC TTC ACT TAC TTT GCA CCG AGT AAT GAG GCT TGG     486
Glu Gly Lys Gly Ser Phe Thr Tyr Phe Ala Pro Ser Asn Glu Ala Trp
        135                 140                 145

GAC AAC TTG GAT TCT GAT ATC CGT AGA GGT TTG GAG AGC AAC GTG AAT     534
Asp Asn Leu Asp Ser Asp Ile Arg Arg Gly Leu Glu Ser Asn Val Asn
    150                 155                 160

GTT GAA TTA CTG AAT GCT TTA CAT AGT CAC ATG ATT AAT AAG AGA ATG     582
Val Glu Leu Leu Asn Ala Leu His Ser His Met Ile Asn Lys Arg Met
165                 170                 175                 180

TTG ACC AAG GAC TTA AAA AAT GGC ATG ATT ATT CCT TCA ATG TAT AAC     630
Leu Thr Lys Asp Leu Lys Asn Gly Met Ile Ile Pro Ser Met Tyr Asn
                185                 190                 195

AAT TTG GGG CTT TTC ATT AAC CAT TAT CCT AAT GGG GTT GTC ACT GTT     678
Asn Leu Gly Leu Phe Ile Asn His Tyr Pro Asn Gly Val Val Thr Val
            200                 205                 210

AAT TGT GCT CGA ATC ATC CAT GGG AAC CAG ATT GCA ACA AAT GGT GTT     726
Asn Cys Ala Arg Ile Ile His Gly Asn Gln Ile Ala Thr Asn Gly Val
        215                 220                 225

GTC CAT GTC ATT GAC CGT GTG CTT ACA CAA ATT GGT ACC TCA ATT CAA     774
Val His Val Ile Asp Arg Val Leu Thr Gln Ile Gly Thr Ser Ile Gln
```

-continued

```
    230                 235                 240

GAC TTC ATT GAA GCA GAA GAT GAC CTT TCA TCT TTT AGA GCA GCT GCC      822
Asp Phe Ile Glu Ala Glu Asp Asp Leu Ser Ser Phe Arg Ala Ala Ala
245                 250                 255                 260

ATC ACA TCG GAC ATA TTG GAG GCC CTT GGA AGA GAC GGT CAC TTC ACA      870
Ile Thr Ser Asp Ile Leu Glu Ala Leu Gly Arg Asp Gly His Phe Thr
                265                 270                 275

CTC TTT GCT CCC ACC AAT GAG GCT TTT GAG AAA CTT CCA CGA GGT GTC      918
Leu Phe Ala Pro Thr Asn Glu Ala Phe Glu Lys Leu Pro Arg Gly Val
            280                 285                 290

CTA GAA AGG ATC ATG GGA GAC AAA GTG GCT TCC GAA GCT CTT ATG AAG      966
Leu Glu Arg Ile Met Gly Asp Lys Val Ala Ser Glu Ala Leu Met Lys
        295                 300                 305

TAC CAC ATC TTA AAT ACT CTC CAG TGT TCT GAG TCT ATT ATG GGA GGA     1014
Tyr His Ile Leu Asn Thr Leu Gln Cys Ser Glu Ser Ile Met Gly Gly
    310                 315                 320

GCA GTC TTT GAG ACG CTG GAA GGA AAT ACA ATT GAG ATA GGA TGT GAC     1062
Ala Val Phe Glu Thr Leu Glu Gly Asn Thr Ile Glu Ile Gly Cys Asp
325                 330                 335                 340

GGT GAC AGT ATA ACA GTA AAT GGA ATC AAA ATG GTG AAC AAA AAG GAT     1110
Gly Asp Ser Ile Thr Val Asn Gly Ile Lys Met Val Asn Lys Lys Asp
                345                 350                 355

ATT GTG ACA AAT AAT GGT GTG ATC CAT TTG ATT GAT CAG GTC CTA ATT     1158
Ile Val Thr Asn Asn Gly Val Ile His Leu Ile Asp Gln Val Leu Ile
            360                 365                 370

CCT GAT TCT GCC AAA CAA GTT ATT GAG CTG GCT GGA AAA CAG CAA ACC     1206
Pro Asp Ser Ala Lys Gln Val Ile Glu Leu Ala Gly Lys Gln Gln Thr
        375                 380                 385

ACC TTC ACG GAT CTT GTG GCC CAA TTA GGC TTG GCA TCT GCT CTG AGG     1254
Thr Phe Thr Asp Leu Val Ala Gln Leu Gly Leu Ala Ser Ala Leu Arg
    390                 395                 400

CCA GAT GGA GAA TAC ACT TTG CTG GCA CCT GTG AAT AAT GCA TTT TCT     1302
Pro Asp Gly Glu Tyr Thr Leu Leu Ala Pro Val Asn Asn Ala Phe Ser
405                 410                 415                 420

GAT GAT ACT CTC AGC ATG GAT CAG CGC CTC CTT AAA TTA ATT CTG CAG     1350
Asp Asp Thr Leu Ser Met Asp Gln Arg Leu Leu Lys Leu Ile Leu Gln
                425                 430                 435

AAT CAC ATA TTG AAA GTA AAA GTT GGC CTT AAT GAG CTT TAC AAC GGG     1398
Asn His Ile Leu Lys Val Lys Val Gly Leu Asn Glu Leu Tyr Asn Gly
            440                 445                 450

CAA ATA CTG GAA ACC ATC GGA GGC AAA CAG CTC AGA GTC TTC GTA TAT     1446
Gln Ile Leu Glu Thr Ile Gly Gly Lys Gln Leu Arg Val Phe Val Tyr
        455                 460                 465

CGT ACA GCT GTC TGC ATT GAA AAT TCA TGC ATG GAG AAA GGG AGT AAG     1494
Arg Thr Ala Val Cys Ile Glu Asn Ser Cys Met Glu Lys Gly Ser Lys
    470                 475                 480

CAA GGG AGA AAC GGT GCG ATT CAC ATA TTC CGC GAG ATC ATC AAG CCA     1542
Gln Gly Arg Asn Gly Ala Ile His Ile Phe Arg Glu Ile Ile Lys Pro
485                 490                 495                 500

GCA GAG AAA TCC CTC CAT GAA AAG TTA AAA CAA GAT AAG CGC TTT ACG     1590
Ala Glu Lys Ser Leu His Glu Lys Leu Lys Gln Asp Lys Arg Phe Thr
                505                 510                 515

ACC TTC CTC AGC CTA CTT GAA GCT GCA GAC TTG AAA GAG CTC CTG ACA     1638
Thr Phe Leu Ser Leu Leu Glu Ala Ala Asp Leu Lys Glu Leu Leu Thr
            520                 525                 530

CAA CCT GGA GAC TGG ACA TTA TTT GTG CCA ACC AAT GAT GCT TTT AAG     1686
Gln Pro Gly Asp Trp Thr Leu Phe Val Pro Thr Asn Asp Ala Phe Lys
        535                 540                 545

GGA ATG ACT AGT GAA GAA AAA GAA ATT CTG ATA CGG GAC AAA AAT GCT     1734
Gly Met Thr Ser Glu Glu Lys Glu Ile Leu Ile Arg Asp Lys Asn Ala
```

-continued 550 555 560

CTT CAA AAC ATC ATT CTT TAT CAC CTG ACA CCA GGA GTT TTC ATT GGA 1782
Leu Gln Asn Ile Ile Leu Tyr His Leu Thr Pro Gly Val Phe Ile Gly
565 570 575 580

AAA GGA TTT GAA CCT GGT GTT ACT AAC ATT TTA AAG ACC ACA CAA GGA 1830
Lys Gly Phe Glu Pro Gly Val Thr Asn Ile Leu Lys Thr Thr Gln Gly
585 590 595

AGC AAA ATC TTT CTG AAA GAA GTA AAT GAT ACA CTT CTG GTG AAT GAA 1878
Ser Lys Ile Phe Leu Lys Glu Val Asn Asp Thr Leu Leu Val Asn Glu
600 605 610

TTG AAA TCA AAA GAA TCT GAC ATC ATG ACA ACA AAT GGT GTA ATT CAT 1926
Leu Lys Ser Lys Glu Ser Asp Ile Met Thr Thr Asn Gly Val Ile His
615 620 625

GTT GTA GAT AAA CTC CTC TAT CCA GCA GAC ACA CCT GTT GGA AAT GAT 1974
Val Val Asp Lys Leu Leu Tyr Pro Ala Asp Thr Pro Val Gly Asn Asp
630 635 640

CAA CTG CTG GAA ATA CTT AAT AAA TTA ATC AAA TAC ATC CAA ATT AAG 2022
Gln Leu Leu Glu Ile Leu Asn Lys Leu Ile Lys Tyr Ile Gln Ile Lys
645 650 655 660

TTT GTT CGT GGT AGC ACC TTC AAA GAA ATC CCC GTG ACT GTC TAT AGA 2070
Phe Val Arg Gly Ser Thr Phe Lys Glu Ile Pro Val Thr Val Tyr Arg
665 670 675

CCC ACA CTA ACA AAA GTC AAA ATT GAA GGT GAA CCT GAA TTC AGA CTG 2118
Pro Thr Leu Thr Lys Val Lys Ile Glu Gly Glu Pro Glu Phe Arg Leu
680 685 690

ATT AAA GAA GGT GAA ACA ATA ACT GAA GTG ATC CAT GGA GAG CCA ATT 2166
Ile Lys Glu Gly Glu Thr Ile Thr Glu Val Ile His Gly Glu Pro Ile
695 700 705

ATT AAA AAA TAC ACC AAA ATC ATT GAT GGA GTG CCT GTG GAA ATA ACT 2214
Ile Lys Lys Tyr Thr Lys Ile Ile Asp Gly Val Pro Val Glu Ile Thr
710 715 720

GAA AAA GAG ACA CGA GAA GAA CGA ATC ATT ACA GGT CCT GAA ATA AAA 2262
Glu Lys Glu Thr Arg Glu Glu Arg Ile Ile Thr Gly Pro Glu Ile Lys
725 730 735 740

TAC ACT AGG ATT TCT ACT GGA GGT GGA GAA ACA GAA GAA ACT CTG AAG 2310
Tyr Thr Arg Ile Ser Thr Gly Gly Gly Glu Thr Glu Glu Thr Leu Lys
745 750 755

AAA TTG TTA CAA GAA GAC ACA CCC GTG AGG AAG TTG CAA GCC AAC AAA 2358
Lys Leu Leu Gln Glu Asp Thr Pro Val Arg Lys Leu Gln Ala Asn Lys
760 765 770

AAA AGT TCA AGG ATC TAGAAGACGA TTAAGGGAAG GTCGTTCTCA GTGAAAATCC 2413
Lys Ser Ser Arg Ile
775

AAAAACCAGA AAAAAATGTT TATACAACCC TAAGTCAATA ACCTGACCTT AGAAAATTGT 2473

GAGAGCCAAG TTGACTTCAG GAACTGAAAC ATCAGCACAA AGAAGCAATC ATCAAATAAT 2533

TCTGAACACA AATTTAATAT TTTTTTTTCT GAATGAGAAA CATGAGGGAA ATTGTGGAGT 2593

TAGCCTCCTG TGGTAAAGGA ATTGAAGAAA ATATAACACC TTACACCCTT TTTCATCTTG 2653

ACATTAAAAG TTCTGGCTAA CTTTGGAATC CATTAGAGAA AAATCCTTGT CACCAGATTC 2713

ATTACAATTC AAATCGAAGA GTTGTGAACT GTTATCCCAT TGAAAAGACC GAGCCTTGTA 2773

TGTATGTTAT GGATACATAA AATGCACGCA AGCCATTATC TCTCCATGGG AAGCTAAGTT 2833

ATAAAAATAG GTGCTTGGTG TACAAAACTT TTTATGATCA AAAGGCTTTG CACATTTCTA 2893

TATGAGTGGG TTTACTGGTA AATTATGTTA TTTTTTACAA CTAATTTTGT ACTCTCAGAA 2953

TGTTTGTCAT ATGCTTCTTG CAATGCATAT TTTTTAATCT CAAACGTTTC AATAAAACCA 3013

TTTTTCAGAT ATAAAGAGAA TTACTTCAAA TTGAGTAATT CAGAAAAACT CAAGATTTAA 3073

-continued

GTTAAAAAGT GGTTTGGACT TGGGAATAGG ACTTTATACC TCTTTCTCGT GCC 3126

( 2 ) INFORMATION FOR SEQ ID NO:4:

( i ) SEQUENCE CHARACTERISTICS:
( A ) LENGTH: 777 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Ala Leu Pro Ala Arg Ile Leu Ala Leu Ala Leu Ala Leu Ala Leu
1 5 10 15

Gly Pro Ala Val Thr Leu Ala Asn Pro Ala Arg Thr Pro Tyr Glu Leu
20 25 30

Val Leu Gln Lys Ser Ser Ala Arg Gly Gly Arg Asp Gln Gly Pro Asn
35 40 45

Val Cys Ala Leu Gln Gln Ile Leu Gly Thr Lys Lys Lys Tyr Phe Ser
50 55 60

Thr Cys Lys Asn Trp Tyr Lys Lys Ser Ile Cys Gly Gln Lys Thr Thr
65 70 75 80

Val Leu Tyr Glu Cys Cys Pro Gly Tyr Met Arg Met Glu Gly Met Lys
85 90 95

Gly Cys Pro Ala Val Leu Pro Ile Asp His Val Tyr Gly Thr Leu Gly
100 105 110

Ile Val Gly Ala Thr Thr Thr Gln Arg Tyr Ser Asp Ala Ser Lys Leu
115 120 125

Arg Glu Glu Ile Glu Gly Lys Gly Ser Phe Thr Tyr Phe Ala Pro Ser
130 135 140

Asn Glu Ala Trp Asp Asn Leu Asp Ser Asp Ile Arg Arg Gly Leu Glu
145 150 155 160

Ser Asn Val Asn Val Glu Leu Leu Asn Ala Leu His Ser His Met Ile
165 170 175

Asn Lys Arg Met Leu Thr Lys Asp Leu Lys Asn Gly Met Ile Ile Pro
180 185 190

Ser Met Tyr Asn Asn Leu Gly Leu Phe Ile Asn His Tyr Pro Asn Gly
195 200 205

Val Val Thr Val Asn Cys Ala Arg Ile Ile His Gly Asn Gln Ile Ala
210 215 220

Thr Asn Gly Val Val His Val Ile Asp Arg Val Leu Thr Gln Ile Gly
225 230 235 240

Thr Ser Ile Gln Asp Phe Ile Glu Ala Glu Asp Asp Leu Ser Ser Phe
245 250 255

Arg Ala Ala Ala Ile Thr Ser Asp Ile Leu Glu Ala Leu Gly Arg Asp
260 265 270

Gly His Phe Thr Leu Phe Ala Pro Thr Asn Glu Ala Phe Glu Lys Leu
275 280 285

Pro Arg Gly Val Leu Glu Arg Ile Met Gly Asp Lys Val Ala Ser Glu
290 295 300

Ala Leu Met Lys Tyr His Ile Leu Asn Thr Leu Gln Cys Ser Glu Ser
305 310 315 320

Ile Met Gly Gly Ala Val Phe Glu Thr Leu Glu Gly Asn Thr Ile Glu
325 330 335

Ile Gly Cys Asp Gly Asp Ser Ile Thr Val Asn Gly Ile Lys Met Val
340 345 350

-continued

Asn Lys Lys Asp Ile Val Thr Asn Asn Gly Val Ile His Leu Ile Asp
355 360 365

Gln Val Leu Ile Pro Asp Ser Ala Lys Gln Val Ile Glu Leu Ala Gly
370 375 380

Lys Gln Gln Thr Thr Phe Thr Asp Leu Val Ala Gln Leu Gly Leu Ala
385 390 395 400

Ser Ala Leu Arg Pro Asp Gly Glu Tyr Thr Leu Leu Ala Pro Val Asn
405 410 415

Asn Ala Phe Ser Asp Asp Thr Leu Ser Met Asp Gln Arg Leu Leu Lys
420 425 430

Leu Ile Leu Gln Asn His Ile Leu Lys Val Lys Val Gly Leu Asn Glu
435 440 445

Leu Tyr Asn Gly Gln Ile Leu Glu Thr Ile Gly Gly Lys Gln Leu Arg
450 455 460

Val Phe Val Tyr Arg Thr Ala Val Cys Ile Glu Asn Ser Cys Met Glu
465 470 475 480

Lys Gly Ser Lys Gln Gly Arg Asn Gly Ala Ile His Ile Phe Arg Glu
485 490 495

Ile Ile Lys Pro Ala Glu Lys Ser Leu His Glu Lys Leu Lys Gln Asp
500 505 510

Lys Arg Phe Thr Thr Phe Leu Ser Leu Leu Glu Ala Ala Asp Leu Lys
515 520 525

Glu Leu Leu Thr Gln Pro Gly Asp Trp Thr Leu Phe Val Pro Thr Asn
530 535 540

Asp Ala Phe Lys Gly Met Thr Ser Glu Glu Lys Glu Ile Leu Ile Arg
545 550 555 560

Asp Lys Asn Ala Leu Gln Asn Ile Ile Leu Tyr His Leu Thr Pro Gly
565 570 575

Val Phe Ile Gly Lys Gly Phe Glu Pro Gly Val Thr Asn Ile Leu Lys
580 585 590

Thr Thr Gln Gly Ser Lys Ile Phe Leu Lys Glu Val Asn Asp Thr Leu
595 600 605

Leu Val Asn Glu Leu Lys Ser Lys Glu Ser Asp Ile Met Thr Thr Asn
610 615 620

Gly Val Ile His Val Val Asp Lys Leu Leu Tyr Pro Ala Asp Thr Pro
625 630 635 640

Val Gly Asn Asp Gln Leu Leu Glu Ile Leu Asn Lys Leu Ile Lys Tyr
645 650 655

Ile Gln Ile Lys Phe Val Arg Gly Ser Thr Phe Lys Glu Ile Pro Val
660 665 670

Thr Val Tyr Arg Pro Thr Leu Thr Lys Val Lys Ile Glu Gly Glu Pro
675 680 685

Glu Phe Arg Leu Ile Lys Glu Gly Glu Thr Ile Thr Glu Val Ile His
690 695 700

Gly Glu Pro Ile Ile Lys Lys Tyr Thr Lys Ile Ile Asp Gly Val Pro
705 710 715 720

Val Glu Ile Thr Glu Lys Glu Thr Arg Glu Glu Arg Ile Ile Thr Gly
725 730 735

Pro Glu Ile Lys Tyr Thr Arg Ile Ser Thr Gly Gly Gly Glu Thr Glu
740 745 750

Glu Thr Leu Lys Lys Leu Leu Gln Glu Asp Thr Pro Val Arg Lys Leu
755 760 765

Gln Ala Asn Lys Lys Ser Ser Arg Ile
770 775

( 2 ) INFORMATION FOR SEQ ID NO:5:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

T G T C C A G A T G 1 0

( 2 ) INFORMATION FOR SEQ ID NO:6:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

T G T C C A G A T G C 1 1

( 2 ) INFORMATION FOR SEQ ID NO:7:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

T G T C C A G A T G A C 1 2

( 2 ) INFORMATION FOR SEQ ID NO:8:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

T G T C C A G A T A 1 0

( 2 ) INFORMATION FOR SEQ ID NO:9:

-continued ( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

T G T C C A G A C G 1 0

( 2 ) INFORMATION FOR SEQ ID NO:10:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

T G T C C A G C C G 1 0

( 2 ) INFORMATION FOR SEQ ID NO:11:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

T G T C C C G C C G 1 0

( 2 ) INFORMATION FOR SEQ ID NO:12:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

T G C C C G G C C G 1 0

( 2 ) INFORMATION FOR SEQ ID NO:13:

( i ) SEQUENCE CHARACTERISTICS:
( A ) LENGTH: 10 base pairs
( B ) TYPE: nucleic acid
( C ) STRANDEDNESS: single -continued ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

T G A T G C A C T C 1 0

( 2 ) INFORMATION FOR SEQ ID NO:14:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

T G A G C T A C T C 1 0

( 2 ) INFORMATION FOR SEQ ID NO:15:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

T G A C T G A C T C 1 0

( 2 ) INFORMATION FOR SEQ ID NO:16:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

C T G A T C C A T G 1 0

( 2 ) INFORMATION FOR SEQ ID NO:17:

( i ) SEQUENCE CHARACTERISTICS:
( A ) LENGTH: 683 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

| | | | | | | | | | | | | | | | |
|---|---|---|---|---|---|---|---|---|---|---|---|---|---|---|---|
| Met | Ala | Leu | Phe | Val | Arg | Leu | Leu | Ala | Leu | Ala | Leu | Ala | Leu | Ala | Leu |
| 1 | | | | 5 | | | | | 10 | | | | | 15 | |
| Gly | Pro | Ala | Ala | Thr | Leu | Ala | Gly | Pro | Ala | Lys | Ser | Pro | Tyr | Gln | Leu |
| | | | 20 | | | | | 25 | | | | | 30 | | |
| Pro | Leu | Gln | His | Ser | Arg | Leu | Arg | Gly | Arg | Gln | His | Gly | Pro | Asn | Val |
| | | 35 | | | | | 40 | | | | | 45 | | | |
| Cys | Ala | Val | Thr | Lys | Val | Ile | Gly | Thr | Asn | Arg | Lys | Tyr | Phe | Thr | Asn |
| | 50 | | | | | 55 | | | | | 60 | | | | |
| Cys | Lys | Gln | Trp | Tyr | Gln | Arg | Lys | Ile | Cys | Gly | Lys | Ser | Thr | Val | Ile |
| 65 | | | | | 70 | | | | | 75 | | | | | 80 |
| Ser | Tyr | Glu | Cys | Cys | Pro | Gly | Tyr | Glu | Lys | Val | Pro | Gly | Glu | Lys | Gly |
| | | | | 85 | | | | | 90 | | | | | 95 | |
| Cys | Pro | Ala | Ala | Leu | Pro | Leu | Ser | Asn | Leu | Tyr | Glu | Thr | Leu | Gly | Val |
| | | | 100 | | | | 105 | | | | | 110 | | | |
| Val | Gly | Ser | Thr | Thr | Thr | Gln | Leu | Tyr | Thr | Asp | Arg | Thr | Glu | Lys | Leu |
| | 115 | | | | | 120 | | | | | 125 | | | | |
| Arg | Pro | Glu | Met | Glu | Gly | Pro | Gly | Ser | Phe | Thr | Ile | Phe | Ala | Pro | Ser |
| 130 | | | | | 135 | | | | | 140 | | | | | 145 |
| Asn | Glu | Ala | Trp | Ala | Ser | Leu | Pro | Ala | Glu | Val | Leu | Val | Ser | Leu | Val |
| | | | | 150 | | | | | 155 | | | | | 160 | |
| Ser | Asn | Val | Asn | Ile | Glu | Leu | Leu | Asn | Ala | Leu | Arg | Tyr | His | Met | Val |
| | | | 165 | | | | | 170 | | | | | 175 | | |
| Gly | Arg | Arg | Val | Leu | Thr | Asp | Glu | Leu | Lys | His | Gly | Met | Thr | Leu | Thr |
| | | 180 | | | | | 185 | | | | | 190 | | | |
| Ser | Met | Tyr | Gln | Asn | Ser | Asn | Ile | Gln | Ile | His | His | Tyr | Pro | Asn | Gly |
| | 195 | | | | | 200 | | | | | 205 | | | | |
| Ile | Val | Thr | Val | Asn | Cys | Ala | Arg | Leu | Leu | Lys | Ala | Asp | His | His | Ala |
| 210 | | | | | 215 | | | | | 220 | | | | | 225 |
| Thr | Asn | Gly | Val | Val | His | Leu | Ile | Asp | Lys | Val | Ile | Ser | Thr | Ile | Thr |
| | | | | 230 | | | | | 235 | | | | | 240 | |
| Asn | Asn | Ile | Gln | Gln | Ile | Ile | Glu | Ile | Glu | Asp | Thr | Phe | Glu | Thr | Leu |
| | | | 245 | | | | | 250 | | | | | 255 | | |
| Arg | Ala | Ala | Val | Ala | Ala | Ser | Gly | Leu | Asn | Thr | Met | Leu | Glu | Gly | Asn |
| | | 260 | | | | | 265 | | | | | 270 | | | |
| Gly | Gln | Tyr | Thr | Leu | Leu | Ala | Pro | Thr | Asn | Glu | Ala | Phe | Glu | Lys | Ile |
| | 275 | | | | | 280 | | | | | 285 | | | | |
| Pro | Ser | Glu | Thr | Leu | Asn | Arg | Ile | Leu | Gly | Asp | Pro | Glu | Ala | Leu | Arg |
| 290 | | | | | 295 | | | | | 300 | | | | | 305 |
| Asp | Leu | Leu | Asn | Asn | His | Ile | Leu | Lys | Ser | Ala | Met | Cys | Ala | Glu | Ala |
| | | | | 310 | | | | | 315 | | | | | 320 | |
| Ile | Val | Ala | Gly | Leu | Ser | Val | Glu | Thr | Leu | Glu | Gly | Thr | Thr | Leu | Glu |
| | | | 325 | | | | | 330 | | | | | 335 | | |
| Val | Gly | Cys | Ser | Gly | Asp | Met | Leu | Thr | Ile | Asn | Gly | Lys | Ala | Ile | Ile |
| | | 340 | | | | | 345 | | | | | 350 | | | |
| Ser | Asn | Lys | Asp | Ile | Leu | Ala | Thr | Asn | Gly | Val | Ile | His | Tyr | Ile | Asp |
| | 355 | | | | | 360 | | | | | 365 | | | | |
| Glu | Leu | Leu | Ile | Pro | Asp | Ser | Ala | Lys | Thr | Leu | Phe | Glu | Leu | Ala | Ala |
| 370 | | | | | 375 | | | | | 380 | | | | | 385 |

-continued

| | | | | | | | | | | | | | | | |
|---|---|---|---|---|---|---|---|---|---|---|---|---|---|---|---|
| Glu | Ser | Asp | Val | Ser 390 | Thr | Ala | Ile | Asp | Leu 395 | Phe | Arg | Gln | Ala | Gly 400 | Leu |
| Gly | Asn | His | Leu 405 | Ser | Gly | Ser | Glu | Arg 410 | Leu | Thr | Leu | Leu | Ala 415 | Pro | Leu |
| Asn | Ser | Val 420 | Phe | Lys | Asp | Gly | Thr 425 | Pro | Pro | Ile | Asp | Ala 430 | His | Thr | Arg |
| Asn | Leu 435 | Leu | Arg | Asn | His | Ile 440 | Ile | Lys | Asp | Gln | Leu 445 | Ala | Ser | Lys | Tyr |
| Leu 450 | Tyr | His | Gly | Gln | Thr 455 | Leu | Glu | Thr | Leu | Gly 460 | Gly | Lys | Lys | Leu | Arg 465 |
| Val | Phe | Val | Tyr | Arg 470 | Asn | Ser | Leu | Cys | Ile 475 | Glu | Asn | Ser | Cys | Ile 480 | Ala |
| Ala | His | Asp | Lys 485 | Arg | Gly | Arg | Tyr | Gly 490 | Thr | Leu | Phe | Thr | Met 495 | Asp | Arg |
| Val | Leu | Thr 500 | Pro | Pro | Met | Gly | Thr 505 | Val | Met | Asp | Val | Leu 510 | Lys | Gly | Asp |
| Asn | Arg 515 | Phe | Ser | Met | Leu | Val 520 | Ala | Ala | Ile | Gln | Ser 525 | Ala | Gly | Leu | Thr |
| Glu 530 | Thr | Leu | Asn | Arg | Glu 535 | Gly | Val | Tyr | Thr | Val 540 | Phe | Ala | Pro | Thr | Asn 545 |
| Glu | Ala | Phe | Arg | Ala 550 | Leu | Pro | Pro | Arg | Glu 555 | Ser | Arg | Arg | Leu | Leu 560 | Gly |
| Asp | Ala | Lys | Glu 565 | Leu | Ala | Asn | Ile | Leu 570 | Lys | Tyr | His | Ile | Gly 575 | Asp | Glu |
| Ile | Leu | Val 580 | Ser | Gly | Gly | Ile | Gly 585 | Ala | Leu | Val | Arg | Leu 590 | Lys | Ser | Leu |
| Gln | Gly 595 | Asp | Lys | Leu | Glu | Val 600 | Ser | Leu | Lys | Asn | Asn 605 | Val | Val | Ser | Val |
| Asn 610 | Lys | Glu | Pro | Val | Ala 615 | Glu | Pro | Asp | Ile | Met 620 | Ala | Thr | Asn | Gly | Val 625 |
| Val | His | Val | Ile | Thr 630 | Asn | Val | Leu | Gln | Pro 635 | Pro | Ala | Asn | Arg | Pro 640 | Gln |
| Glu | Arg | Gly | Asp 645 | Glu | Leu | Ala | Asp | Ser 650 | Ala | Leu | Glu | Ile | Phe 655 | Lys | Gln |
| Ala | Ser | Ala 660 | Phe | Ser | Arg | Ala | Ser 665 | Gln | Arg | Ser | Val | Arg 670 | Leu | Ala | Val |
| Pro | Tyr 675 | Gln | Lys | Leu | Leu | Glu 680 | Arg | Met | Lys | His | | | | | |

( 2 ) INFORMATION FOR SEQ ID NO:18:

( i ) SEQUENCE CHARACTERISTICS:
( A ) LENGTH: 206 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

| | | | | | | | | | | | | | | | |
|---|---|---|---|---|---|---|---|---|---|---|---|---|---|---|---|
| Gly 1 | Glu | Lys | Ser | Leu 5 | Glu | Tyr | Lys | Ile | Arg 10 | Asp | Asp | Pro | Asp | Leu 15 | Ser |
| Gln | Phe | Tyr | Ser | Trp | Leu | Glu | His | Asn | Glu | Val | Ala | Asn | Ser | Thr | Leu |

-continued 20 25 30

Gln Leu Arg Gln Val Thr Val Phe Ala Pro Thr Asn Leu Ala Gln Phe
35 40 45

Asn Tyr Lys Ala Arg Asp Gly Asp Glu Asn Ile Ile Leu Tyr His Met
50 55 60

Thr Asn Leu Ala His Ser Leu Asp Gln Leu Gly His Lys Val Asn Ser
65 70 75 80

Glu Leu Asp Gly Asn Pro Pro Leu Trp Ile Thr Arg Arg Arg Asp Thr
85 90 95

Ile Phe Val Asn Asn Ala Arg Val Leu Thr Glu Arg Ser Asn Tyr Glu
100 105 110

Ala Val Asn Arg His Gly Lys Lys Gln Val Leu His Val Val Asp Ser
115 120 125

Val Leu Glu Pro Val Trp Ser Thr Ser Gly Gln Leu Tyr Asn Pro Asp
130 135 140

Ala Phe Gln Phe Leu Asn Gln Ser Glu Asn Leu Asp Leu Gly Leu His
145 150 155 160

Arg Val Arg Ser Phe Arg Gln Arg Val Phe Gln Asn Gln Lys Gln Asn
165 170 175

Asp Phe Lys Leu Glu Gly Lys His Thr Phe Phe Ile Pro Val Asp Glu
180 185 190

Gly Phe Lys Pro Leu Pro Arg Pro Glu Lys Ile Asp Gln Lys
195 200 205

( 2 ) INFORMATION FOR SEQ ID NO:19:

( i ) SEQUENCE CHARACTERISTICS:
( A ) LENGTH: 200 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

Ala Ala Ala Asp Leu Ala Asp Lys Leu Arg Asp Asp Ser Glu Leu Ser
1 5 10 15

Gln Phe Tyr Ser Leu Leu Glu Ser Asn Gln Ile Ala Asn Ser Thr Leu
20 25 30

Ser Leu Arg Ser Cys Thr Ile Phe Val Pro Thr Asn Glu Ala Phe Gln
35 40 45

Arg Tyr Lys Ser Lys Thr Ala His Val Leu Tyr His Ile Thr Thr Glu
50 55 60

Ala Tyr Thr Gln Lys Arg Leu Pro Asn Thr Val Ser Ser Asp Met Ala
65 70 75 80

Gly Asn Pro Pro Leu Tyr Ile Thr Lys Asn Ser Asn Gly Asp Ile Phe
85 90 95

Val Gly Asn Ala Arg Ile Ile Pro Ser Leu Ser Val Glu Thr Asn Ser
100 105 110

Asp Gly Lys Arg Gln Ile Met His Ile Ile Asp Glu Val Leu Glu Pro
115 120 125

Leu Thr Val Lys Ala Gly His Ser Asp Thr Pro Asn Asn Pro Asn Ala
130 135 140

-continued

| | | | | | | | | | | | | | | | |
|---|---|---|---|---|---|---|---|---|---|---|---|---|---|---|---|
| Leu<br>145 | Lys | Phe | Leu | Lys | Asn<br>150 | Ala | Glu | Glu | Phe | Asn<br>155 | Val | Asp | Asn | Ile | Gly<br>160 |
| Val | Arg | Thr | Tyr | Arg<br>165 | Ser | Gln | Val | Thr | Met<br>170 | Ala | Lys | Lys | Glu | Ser<br>175 | Val |
| Tyr | Asp | Ala<br>180 | Ala | Gly | Gln | His | Thr<br>185 | Phe | Leu | Val | Pro | Val<br>190 | Asp | Glu | Gly |
| Phe | Lys | Leu<br>195 | Ser | Ala | Arg | Ser | Ser<br>200 | | | | | | | | |

What is claimed is:

1. A recombinant nucleic acid comprising a nucleotide sequence encoding the protein TC1 as described in SEQ ID NO:4.

2. The recombinant nucleic acid of claim 1, comprising the sequence provided in FIG. 4 and SEQ ID NO:3.

3. A nucleic acid fragment of the recombinant nucleic acid of claim 1, said nucleic acid fragment being 30 nucleotides or greater in length.

4. A nucleic acid fragment of the recombinant nucleic acid of claim 1, said nucleic acid fragment being 40 nucleotides or greater in length.

5. A nucleic acid fragment of the recombinant nucleic acid of claim 1, said nucleic acid fragment being 50 nucleotides or greater in length.

6. A nucleic acid fragment of the recombinant nucleic acid of claim 1, said nucleic acid fragment having the nucleotide sequence of SEQ ID NO:1.

* * * * *

UNITED STATES PATENT AND TRADEMARK OFFICE

CERTIFICATE OF CORRECTION

PATENT NO. : 5,872,235
DATED : February 16, 1999
INVENTOR(S) : Lan Bo Chen, et al.

It is certified that error appears in the above-identified patent and that said Letters Patent is hereby corrected as shown below:

Column 9,
Line 34, "8 pg", should read -- 80pg --; and

Column 10,
Line 8, "nMdNTP", shoud read -- mM dNTP --.

Signed and Sealed this

Sixth Day of November, 2001

Attest:

*Nicholas P. Godici*

NICHOLAS P. GODICI

*Attesting Officer*

*Acting Director of the United States Patent and Trademark Office*